(12) United States Patent
Wells et al.

(10) Patent No.: US 8,367,048 B2
(45) Date of Patent: *Feb. 5, 2013

(54) SHAMPOO CONTAINING A GEL NETWORK

(75) Inventors: Robert Lee Wells, Cincinnati, OH (US); Douglas Allan Royce, Sunman, IN (US); Eric Scott Johnson, Hamilton, OH (US); Elizabeth Marie Marzonie Elsner, Portage, MI (US); Jennifer Elaine Hilvert, Cincinnati, OH (US); Yingkun Jin, Mason, OH (US); Brian Michael Hurley, Blanchester, OH (US); Teresa Cuasay Manuel, West Chester, OH (US); Benjamin Parker Heath, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1029 days.

This patent is subject to a terminal disclaimer.

(21) Appl. No.: 11/602,705

(22) Filed: Nov. 21, 2006

(65) Prior Publication Data

US 2007/0110700 A1 May 17, 2007

Related U.S. Application Data

(63) Continuation-in-part of application No. 11/228,770, filed on Sep. 16, 2005, which is a continuation-in-part of application No. 10/454,433, filed on Jun. 4, 2003, now Pat. No. 7,303,744.

(60) Provisional application No. 60/385,641, filed on Jun. 4, 2002.

(51) Int. Cl.
*A61Q 5/02* (2006.01)

(52) U.S. Cl. ............... 424/70.19; 424/70.22; 424/70.28

(58) Field of Classification Search .................. None
See application file for complete search history.

(56) References Cited

U.S. PATENT DOCUMENTS

| | | |
|---|---|---|
| 2,396,278 A | 3/1946 | Lind et al. |
| 2,438,091 A | 3/1948 | Lynch et al. |
| 2,486,921 A | 11/1949 | Byerly et al. |
| 2,486,922 A | 11/1949 | Strain et al. |
| 2,528,378 A | 10/1950 | Manheimer et al. |
| 2,658,072 A | 11/1953 | Kosmin et al. |
| 2,694,668 A | 11/1954 | Pricke et al. |
| 2,786,847 A | 3/1957 | Cislak et al. |
| 2,798,053 A | 7/1957 | Brown et al. |
| 2,809,971 A | 10/1957 | Berstein et al. |
| 2,826,551 A | 3/1958 | Geen et al. |
| 3,152,046 A | 10/1964 | Kapral et al. |
| 3,155,591 A | 11/1964 | Hilfer et al. |
| 2,326,733 A | 2/1966 | Karsten et al. |
| 3,236,733 A | 2/1966 | Karsten et al. |
| 3,332,880 A | 7/1967 | Kessler et al. |
| 3,589,999 A | 6/1971 | McRae et al. |
| 3,590,035 A | 6/1971 | Damico et al. |
| 3,753,196 A | 8/1973 | Kurtz et al. |
| 3,761,418 A | 9/1973 | Parran et al. |
| 3,773,770 A | 11/1973 | Damico et al. |
| 3,852,441 A | 12/1974 | Kooistra et al. |
| 3,929,678 A | 12/1975 | Laughlin et al. |
| 3,940,482 A | 2/1976 | Grand et al. |
| 3,958,581 A | 5/1976 | Abegg et al. |
| 3,959,461 A | 5/1976 | Bailey et al. |
| 3,964,500 A | 6/1976 | Drakoff et al. |
| 4,055,655 A | 10/1977 | Maurer et al. |
| 4,089,945 A | 5/1978 | Brinkman et al. |
| 4,152,416 A | 5/1979 | Spitzer et al. |
| 4,161,526 A | 7/1979 | Gorman et al. |
| 4,197,865 A | 4/1980 | Jacquet et al. |
| 4,217,914 A | 8/1980 | Jacquet et al. |
| 4,323,683 A | 4/1982 | Bolich et al. |
| 4,345,080 A | 8/1982 | Bolich et al. |
| 4,364,387 A | 12/1982 | Larkin et al. |
| 4,379,753 A | 4/1983 | Bolich et al. |
| 4,381,919 A | 5/1983 | Jacquet et al. |
| 4,387,090 A | 6/1983 | Bolich et al. |
| 4,422,853 A | 12/1983 | Jacquet et al. |
| 4,470,982 A | 9/1984 | Winkler et al. |
| 4,507,280 A | 3/1985 | Pohl et al. |
| 4,529,586 A | 7/1985 | DeMarco et al. |
| 4,565,647 A | 1/1986 | Llenado et al. |
| 4,608,183 A | 8/1986 | Rossmoore et al. |
| 4,663,158 A | 5/1987 | Wolfram et al. |

(Continued)

FOREIGN PATENT DOCUMENTS

| | | |
|---|---|---|
| CN | 1658830 A | 8/2005 |
| DE | 10005162 A1 | 8/2001 |

(Continued)

OTHER PUBLICATIONS

Eccleston, et al., "Functions of mixed Emulsifiers and Emulsifying Waxes in Dermatological Lotions and Creams", *Colloids and Surfaces*, May 15, 1997, pp. 169-182, vol. 123-124, A. Physicachemicl and Engineering Aspects, Elsevier, Amsterdam, NL, XP000509628.

(Continued)

*Primary Examiner* — Jyothsna Venkat
(74) *Attorney, Agent, or Firm* — Angela K. Haughey

(57) ABSTRACT

Shampoo compositions comprise (a) from about 5% to about 50% of one or more detersive surfactants, by weight of the shampoo composition; (b) a dispersed gel network phase comprising, by weight of the shampoo composition, (i) at least about 0.05% of one or more fatty amphiphiles; (ii) at least about 0.01% of one or more secondary surfactants; and (iii) water; and (c) at least about 20% of an aqueous carrier, by weight of the shampoo composition. A process for preparing a shampoo composition comprises the steps of: (a) combining a fatty amphiphile, a secondary surfactant, and water at a temperature sufficient to allow partitioning of the secondary surfactant and the water into the fatty amphiphile to form a pre-mix; (b) cooling the pre-mix below the chain melt temperature of the fatty amphiphile to form a gel network; (c) adding the gel network to one or more detersive surfactants and an aqueous carrier to form a shampoo composition.

14 Claims, No Drawings

U.S. PATENT DOCUMENTS

| | | | |
|---|---|---|---|
| 4,666,616 A | 5/1987 | Rossmoore et al. | |
| 4,670,430 A | 6/1987 | Imamura et al. | |
| 4,686,254 A | 8/1987 | Lochhead et al. | |
| 4,704,272 A | 11/1987 | Oh | |
| 4,708,863 A | 11/1987 | Bews et al. | |
| 4,788,006 A | 11/1988 | Bolich et al. | |
| 4,834,767 A | 5/1989 | Helioff et al. | |
| 4,885,107 A | 12/1989 | Wetzel et al. | |
| 4,898,585 A | 2/1990 | Borsanyi et al. | |
| 5,034,218 A | 7/1991 | Duvel et al. | |
| 5,057,153 A | 10/1991 | Ruggiero et al. | |
| 5,104,646 A | 4/1992 | Bolich et al. | |
| 5,106,609 A | 4/1992 | Bolich et al. | |
| 5,106,613 A | 4/1992 | Hartnett et al. | |
| 5,114,898 A | 5/1992 | Pinnavaia et al. | |
| 5,154,847 A | 10/1992 | LaPetina et al. | |
| 5,186,928 A | 2/1993 | Birtwistle et al. | |
| 5,202,048 A | 4/1993 | Bartolo et al. | |
| 5,227,156 A | 7/1993 | Weise et al. | |
| 5,248,445 A | 9/1993 | Rizvi et al. | |
| RE34,584 E | 4/1994 | Grote et al. | |
| 5,358,667 A | 10/1994 | Bergmann et al. | |
| 5,462,589 A | 10/1995 | Nicholas et al. | |
| 5,466,425 A | 11/1995 | Adams et al. | |
| 5,478,501 A | 12/1995 | Rau | |
| 5,518,774 A | 5/1996 | Kappock et al. | |
| 5,540,954 A | 7/1996 | Nicholas et al. | |
| 5,562,995 A | 10/1996 | Kappock et al. | |
| 5,614,538 A | 3/1997 | Nelson et al. | |
| 5,674,478 A | 10/1997 | Dodd et al. | |
| 5,696,169 A | 12/1997 | Arima et al. | |
| 5,710,114 A | 1/1998 | Pyles et al. | |
| 5,726,137 A | 3/1998 | Patel et al. | |
| 5,750,122 A | 5/1998 | Evans et al. | |
| 5,756,076 A | 5/1998 | Cervantes et al. | |
| 5,785,962 A * | 7/1998 | Hinz et al. | 424/70.22 |
| 5,798,121 A | 8/1998 | Cauwet et al. | |
| 5,837,661 A | 11/1998 | Evans et al. | |
| 5,853,707 A | 12/1998 | Wells | |
| 5,854,319 A | 12/1998 | O'Lenick et al. | |
| 5,874,476 A | 2/1999 | Hsu et al. | |
| 5,876,705 A | 3/1999 | Uchiyama et al. | |
| 5,880,076 A | 3/1999 | Vermeer et al. | |
| 5,883,154 A | 3/1999 | Kappock et al. | |
| 5,939,059 A | 8/1999 | Franklin et al. | |
| 5,939,203 A | 8/1999 | Kappock et al. | |
| 5,955,066 A | 9/1999 | Sako et al. | |
| 5,965,515 A | 10/1999 | Rau | |
| 5,997,851 A | 12/1999 | Cox et al. | |
| 6,017,562 A | 1/2000 | Kaufman et al. | |
| 6,034,043 A | 3/2000 | Fujiwara et al. | |
| 6,303,109 B1 | 10/2001 | Foerster et al. | |
| 6,309,628 B1 | 10/2001 | Ansmann et al. | |
| 6,333,040 B1 | 12/2001 | Boyxen et al. | |
| RE37,793 E | 7/2002 | Domenico et al. | |
| 6,495,538 B2 | 12/2002 | Fliss et al. | |
| 6,521,238 B1 | 2/2003 | Muller | |
| 6,521,239 B1 | 2/2003 | Breton et al. | |
| RE38,130 E | 6/2003 | Adams | |
| 6,719,967 B1 | 4/2004 | Brown | |
| 6,774,096 B1 | 8/2004 | Paye et al. | |
| 6,908,912 B2 | 6/2005 | Rioux et al. | |
| 7,303,744 B2 * | 12/2007 | Wells et al. | 424/70.28 |
| 2001/0047039 A1 | 11/2001 | McManus et al. | |
| 2002/0012646 A1 | 1/2002 | Royce et al. | |
| 2002/0119113 A1 | 8/2002 | Ellis et al. | |
| 2002/0169283 A1 | 11/2002 | Lu et al. | |
| 2003/0095938 A1 | 5/2003 | Casero et al. | |
| 2003/0119805 A1 | 6/2003 | Fliss et al. | |
| 2003/0130145 A1 | 7/2003 | Patel et al. | |
| 2003/0171231 A1 | 9/2003 | Shana'a et al. | |
| 2003/0185779 A1 | 10/2003 | Mitsumatsu et al. | |
| 2003/0215522 A1 | 11/2003 | Johnson et al. | |
| 2003/0223952 A1 | 12/2003 | Wells et al. | |
| 2003/0224955 A1 | 12/2003 | Ribery et al. | |
| 2004/0058855 A1 | 3/2004 | Schwartz et al. | |
| 2004/0167114 A1 | 8/2004 | Fliss et al. | |
| 2004/0191331 A1 | 9/2004 | Schwartz et al. | |
| 2004/0197294 A1 | 10/2004 | Seipel et al. | |
| 2004/0223941 A1 | 11/2004 | Schwartz et al. | |
| 2004/0234471 A1 | 11/2004 | Corbella | |
| 2004/0266886 A1 | 12/2004 | Seipel et al. | |
| 2005/0031569 A1 | 2/2005 | Seipel et al. | |
| 2005/0143268 A1 | 6/2005 | Midha | |
| 2005/0181067 A1 | 8/2005 | Yokoyama et al. | |
| 2005/0202984 A1 | 9/2005 | Schwartz et al. | |
| 2006/0024256 A1 | 2/2006 | Wells et al. | |
| 2006/0024381 A1 | 2/2006 | Schwartz et al. | |
| 2006/0045861 A1 | 3/2006 | Bejger et al. | |
| 2006/0251605 A1 | 11/2006 | Belmar | |
| 2006/0269501 A1 | 11/2006 | Johnson et al. | |
| 2006/0269502 A1 | 11/2006 | Johnson et al. | |
| 2007/0110696 A1 | 5/2007 | Johnson et al. | |
| 2007/0110700 A1 | 5/2007 | Wells | |
| 2007/0128147 A1 | 6/2007 | Schwartz et al. | |
| 2008/0152611 A1 | 6/2008 | Wells et al. | |
| 2008/0187507 A1 | 8/2008 | Johnson et al. | |

FOREIGN PATENT DOCUMENTS

| | | |
|---|---|---|
| EP | 0037318 A1 | 10/1981 |
| EP | 0077630 | 4/1985 |
| EP | 0555690 | 8/1993 |
| EP | 0627216 A2 | 12/1994 |
| EP | 0976393 A1 | 2/2000 |
| EP | 1123693 | 2/2000 |
| EP | 1082086 | 3/2001 |
| EP | 1161869 | 12/2001 |
| FR | 2478467 | 9/1981 |
| FR | 2593801 | 8/1987 |
| GB | 849433 | 9/1960 |
| GB | 2177108 | 1/1987 |
| GB | 2177108 A | 1/1987 |
| JP | 52/092881 | 8/1977 |
| JP | 6134227 | 5/1994 |
| JP | 7118103 | 5/1995 |
| JP | 2000/103724 | 4/2000 |
| JP | 2001181145 A2 | 7/2001 |
| JP | 2001311099 A2 | 11/2001 |
| JP | 2002/104940 | 4/2002 |
| JP | 2002-104940 | 10/2002 |
| JP | 2004/262805 | 9/2004 |
| JP | 2004-262805 A1 | 9/2004 |
| JP | 2004/292387 | 10/2004 |
| JP | 2004-292387 A | 10/2004 |
| JP | 2004/292390 | 10/2004 |
| JP | 2004-292390 | 10/2004 |
| JP | 2004/307463 | 11/2004 |
| JP | 2004-307463 A | 11/2004 |
| JP | 2005/022983 | 1/2005 |
| JP | 2005-022983 A | 1/2005 |
| JP | 2005/187342 A | 7/2005 |
| JP | 2006063044 A2 | 3/2006 |
| WO | WO-93/08787 A2 | 5/1993 |
| WO | WO 9308787 | 5/1993 |
| WO | WO 9410973 | 5/1994 |
| WO | WO 9501152 | 1/1995 |
| WO | WO 9625913 | 8/1996 |
| WO | WO 9714396 | 4/1997 |
| WO | WO 9847372 | 10/1998 |
| WO | WO 9938475 | 8/1999 |
| WO | WO-99/51199 A1 | 10/1999 |
| WO | WO 9951199 | 10/1999 |
| WO | WO 9959540 | 11/1999 |
| WO | WO 00/66081 | * 11/2000 |
| WO | WO 0066081 | 11/2000 |
| WO | WO-01/00149 A1 | 1/2001 |
| WO | WO 0100149 | 1/2001 |
| WO | WO 01/17492 | * 3/2001 |
| WO | WO 0117492 | 3/2001 |
| WO | WO-01/39735 A1 | 6/2001 |
| WO | WO 0139735 | 6/2001 |
| WO | WO-01/78657 A1 | 10/2001 |
| WO | WO 0178657 | 10/2001 |
| WO | WO 0219977 | 3/2002 |
| WO | WO 0222091 | 3/2002 |
| WO | WO 0232361 | 4/2002 |
| WO | WO 02076422 | 10/2002 |

| | | |
|---|---|---|
| WO | WO 02080943 | 10/2002 |
| WO | WO 03032934 | 4/2003 |
| WO | WO-03/101418 A | 12/2003 |
| WO | WO 03101418 | 12/2003 |
| WO | WO 2005/048959 | 6/2005 |
| WO | WO-2005/048959 A | 6/2005 |

OTHER PUBLICATIONS

Ribeiro, H.M., et al, "Structure and rheology of semisolid o/w creams containing cetyl alcohol/non-ionic surfactant mixed emulsifier and different polymers", International Journal of Cosmetic Science, 2004, pp. 47-59, vol. 26, No. 2, Blackwell Publishing Ltd, XP002413735.

Savic, Snezana et al, "Colloidal Microstructure of binary systems and model creams stabilized with an alkylpolyglucoside non-ionic emulsifier", Colloid Polymer Science, Springer-Verlag, Sep. 28, 2004, p. 439-451, fig 5, vol. 283, XP002413673.

Barry & Rowe, The Characterization by Small Angle X-Ray Scattering of a Gel with a Lamellar Structure, International Journal of Pharmaceuticals, 1989.

Barry & Saunders, Kinetics of Structure Build-up in Self Bodied Emulsions Stabalized by Mixed Emulsifiers, Journal of Colloid Science, vol. 41, 1972.

Barry, B.W., Structure and Rheology of Emulsions Stabalized by Mixed Emulsifiers, British Society of Rheology, 1970.

Benton et al, Phase Behavior and Network Formation in a Cationic Surfactant-Fatty Alcohol System, JAOCS, vol. 64, 1987.

Burgess, J.D., Practical Analysis of Complex Coacervate Systems, Journal of Colloid Science, vol. 140, 1990.

CTFA Cosmetic Ingredient Dictionary, 1982, 3rd Edition, The Cosmetic, Toiletry & Fragrance Association, Inc., Washington, DC (book not included).

Eccleston, G.M., Application of Emulsion Stability Theories to Mobile and Semisolid o/w Emulsions, Cosmetics Magazine, vol. 101, 1986.

Eccleston, G.M., Application of Emulsion Theory to Complex and Real Systems, International Journal of Cosmetic Science, 1985.

Eccleston, G.M., Formulating Cosmetic Emulsions, Cosmetics Magazine, vol. 112, 1997.

Eccleston, G.M., Functions of Mixed Emulsifiers and Emulsifying Waxes in Dermatological Lotions and Creams, Colloids and Surfaces, vol. 123, 1997.

Eccleston, G.M., Microstructural Changes During Storage of Cetostearyl Alcohol/Polyoxyethylene Alkyl Ether Surfactants, University of Strathclyde, 1988.

Eccleston, G.M., Multiple Phase Oil and Water Emulsions, Journal of Cosmetic Chemists, 1990.

Eccleston, G.M., Structure and Rheology of Semisolid o/w Creams Containing Cetyl Alcohol/Non-ionic Surfactant Mixed Emulsifier and Different Polymers, International Journal of Cosmetic Science, 2004.

Eccleston, G.M., Synchrotron X-ray Investigations into the Lamellar Gel Phase Formed in Creams Prepared with Fatty Alcohols, International Journal of Pharmaceuticals, 2000.

Eccleston, G.M., The Influence of Fatty Alcohols on the Structure and Stability of Creams Preapred with Fatty Alcohols, International Journal of Cosmetic Science, 1982.

Encyclopedia of Polymer Science and Engineering, John Wiley & Sons, vol. 15, 1989 (book not included).

Griffin, W.C., Calculation of HLB Values of Non-Ionic Surfactants, Journal of the Society of Cosmetic Chemists; 1954. vol. 5, pp. 249-235.

Korhonen et al, Rheological Properties of Three Component Creams Containing Sorbitan Monoesters as Surfactants, International Journal of Pharmaceuticals, 2002.

Louden et al, A Preliminary Examination of the Structure of Gels and Emulsions Containing Cetostearyl Alcohol, International Journal of Pharmaceuticals, 1985.

McCutcheon, Emulsifiers and Detergents, MC Pub Company, 1989 (book not included).

Noll, W., Chemistry and Technology of Silicones, Academic Press, 1968 (book not included).

Patel et al, Properties of Cetrimide / Cetostearyl Alcohol Ternary Gels; Preparation Effects, International Journal of Pharmaceuticals, 1985.

Savic et al, Colloidal Microstructure of Binary Systems and Model Creams Stablized with an Alkylpolyglucoside Emulsifier, Colloid Polymer Science, vol. 283, 2004.

Saxton, C., Antiplaque Effects and Mode of Action of a Combination of Zinc Citrate and a Nonionic Antimicrobial Agent, Scandinavian Journal, vol. 96, 1988.

Suzuki et al, Secondary Droplet Emulsion: Mechanism & Effects of Liquid Crystal Formation in o/w Emulsion, Journal of Dispersion Science, 1984.

Van Cutsem, Journal of the American Academy of Dermatology, XP-002288119, 1998.

Van Oss, C.J., Coacervation, Complex Coacervation and Flocculation, Journal of Dispersion Science, vol. 9, 1989.

Yoon et al, A Study of Gel Structure in the Nonionic Surfactant / Cetostearyl Alcohol / Water Ternary Systems by Differential Scanning Calorimeter, Journal of Dispersion Science, 1999.

* cited by examiner

SHAMPOO CONTAINING A GEL NETWORK

CROSS REFERENCE TO RELATED APPLICATION

This application is a continuation-in-part of co-pending U.S. application Ser. No. 11/228,770, filed on Sep. 16, 2005, which is a continuation-in-part of prior U.S. application Ser. No. 10/454,433, now granted as U.S. Pat. No. 7,303,744, filed on Jun. 4, 2003; which claims the benefit of U.S. Provisional Application Ser. No. 60/385,641, filed on Jun. 4, 2002.

U.S. application Ser. No. 11/228,770 and U.S. application Ser. No. 10/454,433 are hereby incorporated herein by reference.

FIELD OF THE INVENTION

The present invention relates to a hair cleansing and conditioning shampoo containing a gel network comprising a fatty amphiphile.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair."

A variety of approaches have been developed to alleviate these after-shampoo problems. These approaches range from post-shampoo application of hair conditioners such as leave-on and rinse-off products, to hair conditioning shampoos which attempt to both cleanse and condition the hair from a single product.

In order to provide hair conditioning benefits in a cleansing shampoo base, a wide variety of conditioning actives have been proposed. However, many of these actives have the disadvantage of leaving the hair feeling soiled or coated and of interfering with the cleansing efficacy of the shampoo.

Coacervate formation in a shampoo composition is known to be advantageous for providing conditioning benefits to the hair. The use of cationic polymers to form coacervate is known in the art, such as in PCT publications WO 93/08787 and WO 95/01152. However, these shampoo compositions are good for delivering wet hair conditioning but are not capable of delivering satisfactory dry hair smooth feel.

Based on the foregoing, there is a need for a conditioning shampoo which can provide improved conditioning benefit for dry hair, while not interfering with the cleansing efficacy, nor providing negative feel to the hair when it is dried. Specifically, there is a need to provide long lasting moisturized feel, smooth feel, and manageability control to the hair when the hair is dried, yet not leave the hair feeling greasy, as well as to provide softness and ease of combing when the hair is wet.

None of the existing art provides all of the advantages and benefits of the present invention.

SUMMARY OF THE INVENTION

The present invention is directed to a shampoo composition comprising: (a) from about 5% to about 50% of one or more detersive surfactants, by weight of the shampoo composition; (b) a dispersed gel network phase comprising: (i) at least about 0.05% of one or more fatty amphiphiles, by weight of the shampoo composition; (ii) at least about 0.01% of one or more secondary surfactants, by weight of the shampoo composition; and (iii) water; and (c) at least about 20% of an aqueous carrier, by weight of the shampoo composition.

The present invention also is directed to a process of making the shampoo composition described above.

The present invention is further directed to a method of using the shampoo composition described above.

These and other features, aspects, and advantages of the present invention will become evident to those skilled in the art from a reading of the present disclosure.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

The term "charge density", as used herein, refers to the ratio of the number of positive charges on a polymer to the molecular weight of said polymer.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "polymer" as used herein shall include materials whether made by polymerization of one type of monomer or made by two (i.e., copolymers) or more types of monomers.

The term "shampoo" as used herein means a composition for cleansing and conditioning hair or skin, including scalp, face, and body.

The term "suitable for application to human hair" as used herein means that the compositions or components thereof so described are suitable for use in contact with human hair and the scalp and skin without undue toxicity, incompatibility, instability, allergic response, and the like.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The shampoo compositions of the present invention comprise one or more detersive surfactants, a dispersed gel network phase, and an aqueous carrier. Each of these essential components, as well as preferred or optional components, is described in detail hereinafter.

A. Detersive Surfactant

The shampoo compositions of the present invention comprise one or more detersive surfactants. The detersive surfactant component is included in shampoo compositions of the present invention to provide cleansing performance. The detersive surfactant may be selected from anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. The concentration of the anionic surfactant component in the composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Preferred anionic surfactants suitable for use in the compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with from about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $R^1$—$SO_3$—M wherein $R^1$ is a straight or branched chain, saturated, aliphatic hydrocarbon radical having from about 8 to about 24, preferably from about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having from about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non-limiting example of such an alpha-olefin sulfonate mixture is described in U.S. Pat. No. 3,332,880.

Another class of anionic detersive surfactants suitable for use in the compositions is the beta-alkyloxy alkane sulfonates. These surfactants conform to the formula:

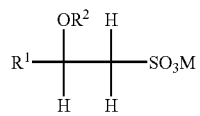

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and combinations thereof.

Suitable zwitterionic or amphoteric detersive surfactants for use in the composition herein include those which are known for use in hair care or other personal cleansing compositions. Concentration of such amphoteric detersive surfactants preferably ranges from about 0.5% to about 20%, preferably from about 1% to about 10%. Non-limiting examples of suitable zwitterionic or amphoteric surfactants are described in U.S. Pat. Nos. 5,104,646 and 5,106,609, both to Bolich Jr. et al.

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The compositions of the present invention may further comprise additional surfactants for use in combination with the anionic detersive surfactant component described hereinbefore. Suitable additional surfactants include cationic and nonionic surfactants.

Cationic surfactants suitable for use in the present invention include quaternary ammonium salts or amido-amines having at least one fatty chain containing at least about 8 carbon atoms and mixture thereof.

Suitable quaternary ammonium salts have the following general formula:

$$N^+(R_1R_2R_3R_4)X^-$$

wherein $R_1$ is selected from linear and branched radicals comprising from about 8 to about 30 carbon atoms; $R_2$ is selected from linear and branched radicals comprising from about 8 to 30 carbon atoms or the same group as radicals $R_3$ and $R_4$; $R_3$ and $R_4$ are independently selected from linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy, and alkylamide radicals; and X— is an anion selected from halides such as chloride, bromide, and iodide, $(C_2-C_6)$ alkyl sulphates, such as methyl sulphate, phosphates, alkyl, and alkylaryl sulphonates, and anions derived from organic acids, such as acetate and lactate.

Non-limiting examples of such suitable cationic surfactants include cetrimonium chloride, stearimonium chloride, behentrimonium chloride, behenamidopropyltrimonium methosulfate, stearamidopropyltrimonium chloride, arachidtrimonium chloride, and mixtures thereof.

Suitable amido-amine cationic surfactants have the following general formula:

$$R'_1—CONH(CH_2)nNR'_2R'_3$$

wherein $R'_1$ is selected from linear and branched radicals comprising about 8 to about 30 carbon atoms; $R'_2$ and $R'_3$ are independently selected from hydrogen, linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy and alkylamide radicals; and n is an integer from about 1 to about 4.

Non-limiting examples of such suitable amido-amines include stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Suitable nonionic surfactants include nonionic surfactants having an HLB of 7 or more and comprising one or more polyethyleneoxide chains wherein each polyethyleneoxide chain contains on average at least about 5 ethylene oxide units.

Nonionic surfactants comprising one or more polyethyleneoxide chain wherein each polyethyleneoxide chain contains on average at least about 5 ethylene oxide units include polyoxyethylene alkyl ethers, polyethyleneglycol fatty acid esters, polyoxyethylene castor oil, polyoxyethylene hydrogenated castor oil, polyoxyethylene fatty amides and their monoethanolamine and diethanolamine derivatives, and polyethoxylated fatty amines, with a number of ethylene oxide groups of at least about 50, and mixtures thereof.

Among preferred nonionic surfactants comprising one or more polyethyleneoxide chain include polyoxyethylene alkyl ethers having at least about 5, preferably from about 10 to 20, ethylene oxide units. Examples of such nonionic surfactants are steareth-10 and steareth-15.

Also suitable for use as nonionic surfactants are nonionic surfactants having an HLB of 7 or more which are free of polyethyleneoxide chains. Nonionic surfactants free of polyethyleneoxide chains include polyglycerolated fatty acids, polyglycerolated fatty amides, polyglycerolated alkyl phenols, polyglycerolated α-diols, polyglycerolated alcohols, alkyl polyglucosides, and sugar esters. Preferably, suitable nonionic surfactants free of polyethyleneoxide chains are selected from alkyl polyglucosides, sugar esters, polyglyceryl fatty acid esters, alkyl polyglyceryl ethers, and mixtures thereof.

Additionally, among suitable nonionic surfactants are alkyl polysaccharide (APS) surfactants such as the alkyl polyglycosides. Such surfactants are described in U.S. Pat. No. 4,565,647 to Llenado, issued Jan. 21, 1986, which discloses APS surfactants having a hydrophobic group with about 6 to about 30 carbon atoms and polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

Also among suitable nonionic surfactants are polyethylene glycol (PEG) glyceryl fatty esters, such as those of the formula $R(O)OCH_2CH(OH)CH_2(OCH_2CH_2)_nOH$, wherein n is from about 5 to about 200, preferably from about 20 to about 100, and R is an aliphatic hydrocarbyl having from about 8 to about 20 carbon atoms.

Any such surfactant known in the art for use in hair or personal care products may be used, provided that the additional surfactant is also chemically and physically compatible with the essential components of the composition, or does not otherwise unduly impair product performance, aesthetics or stability. The concentration of the additional surfactants in the composition may vary with the cleansing or lather performance desired, the optional surfactant selected, the desired product concentration, the presence of other components in the composition, and other factors well known in the art.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

B. Dispersed Gel Network Phase

The shampoo compositions of the present invention comprise a dispersed gel network phase comprising a fatty amphiphile. The gel network phase is included in shampoo compositions of the present invention to provide conditioning benefits. As used herein, the term "gel network" refers to a lamellar or vesicular solid crystalline phase which comprises at least one fatty amphiphile as specified below, at least one secondary surfactant as specified below, and water or other suitable solvents. The lamellar or vesicular phase comprises bi-layers made up of a first layer comprising the fatty amphiphile and the secondary surfactant and alternating with a second layer comprising the water or other suitable solvent. The term "solid crystalline", as used herein, refers to the structure of the lamellar or vesicular phase which forms at a temperature below the chain melt temperature of the layer in the gel network comprising the one or more fatty amphiphiles, the chain melt temperature being at least about 27° C. The chain melt temperature may be measured by differential scanning calorimetry, a method of which is described in the Examples below.

Gel networks which comprise, for example, fatty alcohols have been used for years in cosmetic creams and hair conditioners. Such cosmetic creams and hair conditioners, however, typically contain very low amounts, if any, of detersive surfactant. Thus, such known products do not provide a combination of cleansing and conditioning to the hair or skin.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International, Vol. 7*, 63-70 (1986).

In an embodiment of the present invention, the dispersed gel network phase is pre-formed. The term "pre-formed", as used herein, means that the mixture of the fatty amphiphile, secondary surfactant, and water or other suitable solvent is substantially a solid crystalline phase when added to the other components of the shampoo composition.

According to this embodiment of the present invention, the gel network component of the present invention is prepared as a separate pre-mix, which, after being cooled, is subsequently incorporated with the detersive surfactant and the other components of the shampoo composition. More specifically, the gel network component of the present invention may be prepared by heating the fatty amphiphile, the secondary surfactant, and water to a level in the range of about 75° C. to about 90° C. and mixing. This mixture is cooled to a level in the range of about 27° C. to about 35° C. by, for example, passing the mixture through a heat exchanger. As a result of this cooling step, the fatty amphiphile and the secondary surfactant crystallize to form a solid crystalline gel network.

Alternative methods of preparing the gel network component include sonication and/or milling of the fatty amphiphile, the secondary surfactant, and water, while these components are heated, to reduce the particle size of the melted fatty amphiphile phase. This results in an increase in surface area of the fatty amphiphile phase, which allows the secondary surfactant and the water to swell the fatty amphiphile phase. Another suitable variation in preparing the gel network includes heating and mixing the fatty amphiphile and the secondary surfactant first, and then adding that mixture to the water.

The cooled and pre-formed gel network component subsequently is added to the other components of the shampoo composition, including the detersive surfactant component. While not intending to be limited by theory, it is believed that incorporation of the cooled and pre-formed gel network component with the detersive surfactant and other components of the shampoo composition allows the formation of a substantially equilibrated lamellar dispersion ("ELD") in the final shampoo composition. The ELD is a dispersed lamellar or vesicular phase resulting from the pre-formed gel network component substantially equilibrating with the detersive surfactants, water, and other optional components, such as salts, which may be present in the shampoo composition. This equilibration occurs upon incorporation of the pre-formed gel network component with the other components of the shampoo composition and is effectively complete within about 24 hours after making. Shampoo compositions in which the ELD is formed provide hair with improved wet and dry conditioning benefits. Further, the ELD does not form if the components which comprise the gel network component (i.e., the fatty amphiphile and the secondary surfactant combined with water) are added as individual components together with the other components of the shampoo composition in one mixing step, and not as a separate cooled pre-formed gel network component.

The presence of the gel network in the pre-mix and in the final shampoo composition in the form of the ELD can be confirmed by means known to one of skill in the art, such as X-ray analysis, optical microscopy, electron microscopy, and differential scanning calorimetry. Methods of X-ray analysis and differential scanning calorimetry are described in the Examples below.

In an embodiment of the present invention, the weight ratio of -the fatty amphiphile to the secondary surfactant in the gel network component is greater than about 1:9, preferably greater than about 1:5 to about 100:1, more preferably greater than about 1:1 to about 50:1, and even more preferably greater than about 2:1 to about 10:1.

The shampoo composition of the present invention comprise a gel network in an amount greater than about 0.1%, preferably from about 1% to about 60%, and more preferably from about 5% to about 40%, by weight of the shampoo composition.

1. Fatty Amphiphile

The gel network component of the present invention comprises at least one fatty amphiphile. As used herein, "fatty amphiphile" refers to a compound having a hydrophobic tail group of $R_1$ as defined below and a hydrophilic head group which does not make the compound water soluble, wherein the compound also has a net neutral charge at the pH of the shampoo composition. The term "water soluble", as used herein, means that the material is soluble in water in the present composition. In general, the material should be soluble at 25° C. at a concentration of 0.1% by weight of the water solvent, preferably at 1%, more preferably at 5%, more preferably at 15%.

The fatty amphiphile of the present invention may be characterized as a compound having a Hydrophilic-Lipophilic Balance ("HLB") of 6 or less. The HLB, as used herein, is the standard HLB according to Griffin, J. Soc. Cosm. Chem., vol. 5, 249 (1954).

The shampoo compositions of the present invention comprise fatty amphiphile as part of the pre-formed dispersed gel network phase in an amount from about 0.05% to about 14%, preferably from about 0.5% to about 10%, and more preferably from about 1% to about 8%, by weight of the shampoo composition.

According to the present invention, suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741> "Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

According to the present invention, suitable fatty amphiphiles have a hydrophobic tail group of $R_1$. As used herein, $R_1$ is an alkyl, alkenyl (containing up to 3 double bonds), alkyl aromatic, or branched alkyl group of $C_{12}$-$C_{70}$ length. Non-limiting examples of alkyl, alkenyl, or branched alkyl groups suitable for the fatty amphiphiles of the present invention include lauryl, tridecyl, myristyl, pentadecyl, cetyl, heptadecyl, stearyl, arachidyl, behenyl, undecylenyl, palmitoleyl, oleyl, palmoleyl, linoleyl, linolenyl, arahchidonyl, elaidyl, elaeostearyl, erucyl, isolauryl, isotridecyl, isomyristal, isopentadecyl, petroselinyl, isocetyl, isoheptadecyl, isostearyl, isoarachidyl, isobehnyl, gadoleyl, brassidyl, and technical-grade mixture thereof.

As used herein, $R_1$ also may be a branched alkyl group prepared by alkaline condensation of alcohols to give higher molecular weight, branched isoalcohols. These branched isoalcohols are referred to in the art as Guerbet alcohols.

$R_1$ may be alkyl, alkenyl or branched carbon chains of vegetable origin, such as wheat germ, sunflower, grape seed, sesame, maize, apricot, castor, avocado, olive, soybean, sweet almond, palm, rapeseed, cotton seed, hazelnut, macadamia, karite, jojoba, alfalfa, poppy, pumpkinseed, sesame, cucumber, blackcurrant, evening primrose, millet, barley, quinoa, rye, safflower, candlenut, passion flower or musk rose oil, and karite butter.

Suitable fatty amphiphiles of the present invention also have a hydrophilic head group which does not make the compound water soluble, such as in compounds having an HLB of 6 or less. Non-limiting examples of classes of compounds having such a hydrophilic head group include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids.

To form the gel network component of the present invention, individual fatty amphiphile compounds or combinations of two or more different fatty amphiphile compounds may be selected. The following provides non-limiting examples of classes of compounds from which one or more fatty amphiphiles suitable for use in the present invention may be selected.

a. Fatty Alcohols/Alkoxylated Fatty Alcohol Ethers

Fatty amphiphiles of the present invention may be selected from fatty alcohol compounds or alkoxylated fatty alcohol ether compounds according to the following formula:

wherein $R_1$ is as described above; $R_2$ is a $C_1$-$C_5$ carbon chain which may be branched or hydroxy substituted; and k is a number ranging from about 0 to about 5.

The fatty alcohols useful herein are those having from about 12 to about 60 carbon atoms, preferably from about 16 to about 60 carbon atoms. These fatty alcohols may be straight or branched chain alcohols and may be saturated or unsaturated. Non-limiting examples of suitable fatty alcohols include cetyl alcohol, stearyl alcohol, arachidyl alcohol, behenyl alcohol, C20-40 alcohols, C30-50 alcohols, C40-60 alcohols, and mixtures thereof.

Suitable alkoxylated fatty alcohol ethers include addition products of 1 to 5 mol of ethylene oxide with a linear fatty alcohol having about 12 to about 60 carbon atoms, which are all adducts obtainable by the known industrial oxyethylation processes. Also suitable are the polyethylene oxide condensates of alkyl phenols, for example, the condensation products of alkyl phenols having an alkyl group containing from about 12 to about 60 carbon atoms in either a straight chain or branched chain configuration, with ethylene oxide, wherein the ethylene oxide is present in amounts equal to from about 1 to about 5 moles of ethylene oxide per mole of alkyl phenol. Further suitable alkoxylated fatty alcohol ethers include those derived from the condensation of ethylene oxide with the product resulting from the reaction of propylene oxide and ethylene diamine products.

Non-limiting examples of suitable alkoxylated fatty alcohol ethers include steareth-2, beheneth-2, beheneth-5, beheneth-10, C20-40 Pareth-3, C20-40 Pareth-10, C30-50 Pareth-3, and C30-50-Pareth-10.

b. Di-Fatty Ethers

Fatty amphiphiles of the present invention may be selected from di-fatty ether compounds according to the following formula:

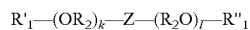

wherein $R_1$ is as described above; $R_2$ is a $C_1$-$C_5$ carbon chain which can be branched or hydroxy substituted; k and l each is independently a number such that the sum (k+l) has a value ranging from 1 to 30; and Z is an ether (i.e., —O—) or an amine (i.e., —NR$_2$—, wherein $R_2$ is as described immediately above).

Compounds of the above formula in which Z is an ether (i.e., dialkyl oxyethyl ethers) may be prepared by esterification processes, which are known in the art, of fatty alcohols and fatty alkyl oxyethanols. Compounds of the above formula in which Z is an amine group may be obtained, for example, from triethanolamine by O-alkylation with 2 mol of a sulfuric half-ester salt of a $C_{12}$-$C_{60}$ fatty alcohol, according to a process for the preparation of ether amines described in DE 35 04 242.

Non-limiting examples of suitable di-fatty ether compounds include dicetylstearyl ether, dicetylstearyl dioxyethyl ether, and N,N-bis(2-cetylstearyl-oxyethyl)aminoethanol.

c. Fatty Amides/Fatty Alkanolamides/Fatty Alkoxylated Amides

Fatty amphiphiles of the present invention also may be selected from fatty amide compounds according to the following formula:

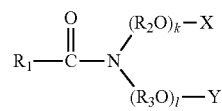

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; and X and Y are each independently selected from hydrogen, a $C_1$-$C_4$ carbon chain which can be branched or hydroxy substituted, morpholine, or a $C_5$-$C_{50}$ carbon chain bonded via an amide, ester, or ether linkage.

Non-limiting examples of suitable fatty amides, fatty alkanolamides or fatty alkoxylated amides include Cocamide, Cocamide Methyl MEA, Cocoyl Glutamic Acid, Erucamide, Lauramide, Oleamide, Palmitamide, Stearamide, Stearyl Erucamide, Behenamide DEA, Behenamide MEA, Cocamide DEA, Cocamide MEA, Cocamide MIPA, Hydroxyethyl Stearamide-MIPA, Hydroxypropyl Bisisostearamide MEA, Hydroxypropyl Bislauramide MEA, Hydroxystearamide MEA, Isostearamide DEA, Isostearamide MEA, Isostearamide MIPA, Lauramide DEA, Lauramide MEA, Lauramide MIPA, Myristamide DEA, Myristamide MEA, Myristamide MIPA, Palmamide DEA, Palmamide MEA, Palmamide MIPA, Palmitamide DEA, Palmitamide MEA, PEG-20 Cocamide MEA, Stearamide AMP, Stearamide DEA, Stearamide DEA-Distearate, Stearamide DIBA-Stearate, Stearamide MEA, Stearamide MEA-Stearate, Stearamide MIPA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PEG-9 Oleamide, PEG-4 Stearamide, PEG-10 Stearamide, PPG-2 Cocamide, PPG-2 Hydroxyethyl Cocamide, PPG-2 Hydroxyethyl Coco/Isostearamide, Ceramide 1, Ceramide 2, Ceramide 3, Ceramide 4, and Ceramide 5.

d. Fatty Carbamates

Fatty amphiphiles of the present invention may be selected from fatty carbamate compounds according to the following formula:

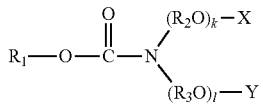

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; and X and Y each is independently selected from hydrogen, a $C_1$-$C_4$ carbon chain which can be branched or hydroxy substituted, morpholine, or a $C_5$-$C_{50}$ carbon chain bonded via an amide, ester, or ether linkage.

Non-limiting examples of suitable fatty carbamates include cetyl carbamate, stearyl carbamate, PEG-2 stearyl carbamate, PEG-4 stearyl carbmate, and behenyl carbamate.

e. Fatty Alkylamido Alkylamines

Fatty amphiphiles of the present invention also may be selected from fatty alkylamido alkylamine compounds according to the following formula:

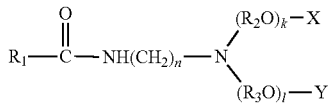

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently selected from hydrogen, a $C_1$-$C_4$ carbon chain which can be branched or hydroxy substituted, morpholine, or a $C_5$-$C_{50}$ carbon chain bonded via an amide, ester, or ether linkage; and n is a number ranging from about 1 to about 4.

Non-limiting examples of suitable fatty alkylamido alkylamine compounds include stearamidoethyl diethanolamine, stearamidopropyl morpholine, stearamidopropyl dimethylamine stearate, stearamidopropyl dimethylamine, stearamidoethyl diethylamine, stearamidoethyl diethanolamine, isostearamidomorpholine stearate, behenamidopropyldimethylamine, behenamidopropyldiethylamine, behenamidoethyldiethyl-amine, cocamidopropyl dimethylamine, behenamidoethyldimethylamine, arachidamidopropyldimethylamine, arachidamido-propyidiethylamine, arachidamidoethyidiethylamine, arachidamidoethyidimethylamine, and mixtures thereof.

f. Fatty Amines/Fatty Alkanolamines/Fatty Alkoxylated Amines

Fatty amphiphiles of the present invention further may be selected from fatty amine compounds according to the following formula:

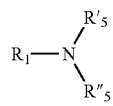

wherein $R_1$ is as described above; and $R'_5$ and $R''_5$ are independently hydrogen or a $C_1$-$C_5$ carbon chain which can be branched or hydroxy substituted.

Additionally, fatty amphiphiles of the present invention may be selected from fatty alkoxylated amine compounds according to either one of the following formulas:

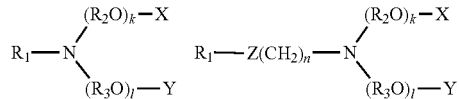

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently hydrogen, a $C_1$-$C_4$ carbon chain which can be branched or hydroxy substituted, morpholine, or a $C_5$-$C_{50}$ carbon chain bonded via amide, ester, or ether linkage; n is a number ranging from about 1 to about 4; and Z is an ether (i.e., —O—) or an amine (i.e., —NH—).

Primary, secondary, and tertiary fatty amines are useful. Suitable fatty alkoxylated amine compounds include addition products of ethylene oxide with a linear fatty alkylamine having 12 to 60 carbon atoms, all of which are adducts obtainable by known industrial processes and which are commercially available.

Non-limiting examples of suitable fatty amine and fatty alkoxylated amine compounds include diethyllauramine, dicocamine, dimethylcocamine amine cetamine, stearamine, oleamine, behenamine, dimethylbehenamine amine, diethylbehenamine, dibehenylamine N-lauryl diethanolamine. TEA-diricinoleate, TEA-lauryl ether, diethylaminoethyl PEG-5 cocoate, diethylaminoethyl PEG-5 laurate, hydroxyethyl isostearyloxy isopropanolamine, PEG-2 cocamine, PEG-5 cocamine, PEG-10 cocamine, PEG-5 isodecyloxypropylamine, PEG-2 lauramine, PEG-2 oleamine, PEG-5 oleamine, PEG-10 oleamine, PEG-2 stearamine, PEG-5 stearamine, PEG-10 stearamine, PPG-2 cocamine, PPG-2 hydrogenated tallowamine, PPG-2 tallowamine, and PPG-3 tallow aminopropylamine.

g. Fatty Amine Oxides

Fatty amphiphiles of the present invention also may be selected from fatty amine oxide compounds according to the following formula:

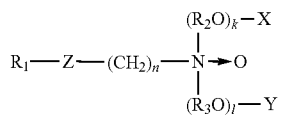

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently hydrogen, a $C_1$-$C_4$ carbon chain which can be branched or hydroxy substituted, morpholine, or a $C_5$-$C_{50}$ carbon chain bonded via an amide, ester, or ether linkage; Z is an ether (i.e., —O—) or an amide (i.e., —C(O)—NH—) linkage; and n is a number ranging from about 1 to about 4. In accord with known convention, the arrow in the above formula is representative of a semi-polar bond.

Non-limiting examples of suitable amine oxide compounds include dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl C12-15 alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl C12-15 alkoxypropylamine oxide, lauramine oxide, myristamine oxide, myristyl/cetyl amine oxide, oleamidopropylamine oxide, oleamine oxide, palmitamine oxide, PEG-3 lauramine oxide, potassium trisphosphonomethylamine oxide, stearamine oxide, and tallowamine oxide.

h. Fatty Acid/Alkoxylated Fatty Acid

Fatty amphiphiles of the present invention also may be selected from fatty acid or alkoxylated fatty acid compounds according to the following formula:

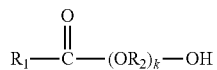

wherein $R_1$ is as described above; $R_2$ is a $C_1$-$C_5$ carbon chain which can be branched or hydroxy substituted; and k is a number ranging from about 0 to about 5.

Non-limiting examples of suitable fatty acids and alkoxylated fatty acids include behenic acid, C10-40 hydroxyalkyl acid, C32-36 isoalkyl acid coconut acid, erucic acid, hydroxystearic acid, lauric acid, linoleic acid, myristic acid, oleic acid, palmitic acid, PEG-8 behenate, PEG-5 cocoate, PEG-10 cocoate, PEG-2 laurate, PEG-4 laurate PEG-6 laurate, PEG-8 laurate, PEG-9 laurate, PEG-10 laurate, PEG-7 oleate, PEG-2 stearate, PEG-3 stearate, PEG-4 stearate, PEG-5 stearate, PEG-6 stearate, PEG-7 stearate, PEG-8 stearate, PEG-9 stearate, PEG-10 stearate, polyglyceryl-2-PEG-4 stearate, PPG-2 isostearate, and PPG-9 laurate.

i. Fatty Esters

Fatty amphiphiles of the present invention may be selected from fatty ester compounds according to the following formula:

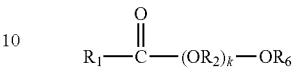

wherein $R_1$ is as described above; $R_2$ is a $C_1$-$C_5$ carbon chain which can be branched or hydroxy substituted; k is a number ranging from about 1 to about 5; and R6 is a $C_1$-$C_{40}$ carbon chain or an alkylcarbonyl (i.e.,

wherein $R_7$ is a $C_1$-$C_{40}$ carbon chain).

These suitable fatty esters include esters with hydrocarbyl chains derived from fatty acids or alcohols (e.g., mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Non-limiting examples of suitable fatty ester compounds include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Fatty amphiphiles of the present invention also may be selected from other fatty ester compounds according to the following formula:

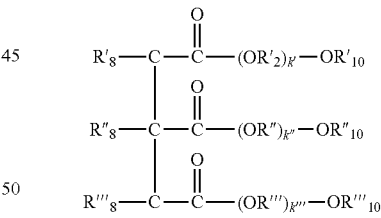

wherein $R'_8$, $R''_8$, and $R'''_8$ each is independently selected from hydrogen, hydroxy, or a $C_1$-$C_4$ carbon chain which can be branched or hydroxy substituted; k', k'', and k''' each is independently a number such that the sum (k'+k''+k''') has a value ranging from 0 to 15; $R'_2$, $R''_2$, and $R'''_2$ each is independently selected from a $C_1$-$C_5$ carbon chain which can be branched or hydroxy substituted; and where $R'_{10}$, $R''_{10}$, $R'''_{10}$ each is independently selected form hydrogen or $R_1$, where $R_1$ is as defined above, provided that at least one of $R'_{10}$, $R''_{10}$, and $R'''_{10}$ is a $R_1$ group.

Still other suitable fatty esters are di- and tri-alkyl and alkenyl esters of carboxylic acids, such as esters of $C_4$ to $C_8$ dicarboxylic acids (e.g., $C_1$ to $C_{22}$ esters, preferably $C_1$ to $C_6$, of succinic acid, glutaric acid, and adipic acid). Specific non-limiting examples of di- and tri- alkyl and alkenyl esters of carboxylic acids include isocetyl stearyol stearate, stearyl citrate, distearyl citrate and tristearyl citrate.

Fatty amphiphiles of the present invention further may be selected from other fatty ester compounds according to the following formula:

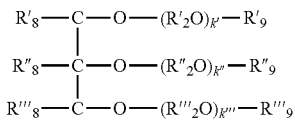

wherein $R'_2$, $R''_2$, and $R'''_2$ each is independently selected from a $C_1$-$C_5$ carbon chain which can be branched or hydroxy substituted; $R'_8$, $R''_8$, and $R'''_8$ each is independently selected from hydrogen, hydroxy, or $C_1$-$C_4$ carbon chain which can be branched or hydroxy substituted; k', k", and k'" each is independently a number such that the sum (k'+k"+k'") has a value ranging from 0 to 15; and $R'_9$, $R''_9$, and $R'''_9$ each is independently selected from hydrogen or alkylcarbonyl (i.e.,

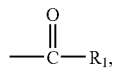

wherein $R_1$ is as described above), provided that at least one of $R'_9$, $R''_9$, and $R'''_9$ is a

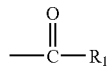

group.

Other suitable fatty esters are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester.

Still other fatty esters suitable for use in the compositions of the present invention are glycerides, including, but not limited to, mono-, di-, and tri-glycerides, preferably mono- and di-glycerides, more preferably mono-glycerides. For use in the compositions described herein, the glycerides are preferably the mono-, di-, and tri-esters of glycerol and long chain carboxylic acids, such as $C_{12}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

j. Fatty Phosphorus Compounds

Fatty amphiphiles of the present invention may be selected from fatty phosphorus compounds according to the following formula:

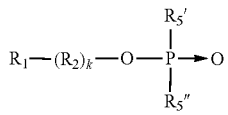

wherein $R_1$ is as described above; $R_2$ is a $C_1$-$C_5$ carbon chain which can be branched or hydroxy substituted; k is a number ranging from about 0 to about 5; and $R_5$ is hydrogen or a $C_1$-$C_4$ carbon chain which can be branched or hydroxy substituted. In accord with known convention, the arrow in the above formula is representative of a semi-polar bond.

Non-limiting examples of suitable fatty phosphorus compounds include dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl) phosphine oxide, tetradecylmethyl-2-hydroxypropylphosphine oxide, oleyldimethylphosphine oxide, and 2-hydroxydodecyldimethylphosphine oxide.

k. Fatty Sorbitan Derivatives

Fatty amphiphiles of the present invention also may be selected from fatty sorbitan derivative compounds according to the following formula:

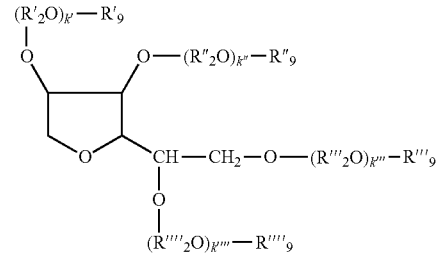

wherein $R'_2$, $R''_2$, $R'''_2$, and $R''''_2$ each is independently a $C_1$-$C_5$ carbon chain which can be branched or hydroxy substituted; $R'_9$, $R''_9$, $R'''_9$, and $R''''_9$ each is independently hydrogen or alkylcarbonyl (i.e.,

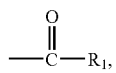

wherein $R_1$ is as described above), provided that at least one of $R'_9$, $R''_9$, $R'''_9$, and $R''''_9$ is a

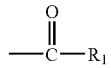

group; and k', k", k'", and k"" each is independently a number such that the sum (k'+k"+k'"+k"") has a value ranging from 0 to 20.

Non-limiting examples of suitable fatty sorbitan derivatives include PEG-20 sorbitan cocoate, PEG-2 sorbitan isostearate, PEG-5 sorbitan isostearate, PEG-20 sorbitan isostearate, PEG-10 sorbitan laurate, PEG-3 sorbitan oleate, PEG-6 sorbitan oleate, PEG-20 sorbitan oleate, PEG-3 sorbitan stearate, PEG-4 sorbitan stearate, PEG-6 sorbitan stearate, PEG-4 sorbitan triisostearate, PEG-20 sorbitan triisostearate, PEG-2 sorbitan trioleate, PEG-3 sorbitan tristearate, polyglyceryl-2 sorbitan tetraethylhexanoate, sorbitan caprylate, sorbitan cocoate, sorbitan diisostearate, sorbitan dioleate, sorbitan distearate, sorbitan isostearate, sorbitan laurate, sorbitan oleate, sorbitan olivate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, and sorbitan undecylenate.

l. Sucrose Polyesters

Fatty amphiphiles of the present invention may be selected from sucrose polyester compounds according to the following formula:

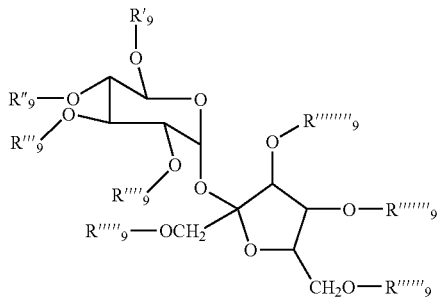

wherein R'$_9$, R''$_9$, R'''$_9$, R''''$_9$, R'''''$_9$, R''''''$_9$, R'''''''$_9$, and R''''''''$_9$ each is hydrogen or alkylcarbonyl (i.e.,

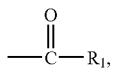

wherein R$_1$ is as described above), provided that at least one of R'$_9$, R''$_9$, R'''$_9$, R''''$_9$, R'''''$_9$, R''''''$_9$, R'''''''$_9$, and R''''''''$_9$ is a

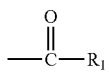

group.

Non-limiting examples of suitable sucrose polyester compounds include Sucrose Cocoate, Sucrose Dilaurate, Sucrose Distearate, Sucrose Hexaerucate, Sucrose Hexaoleate/Hexapalmitate/Hexastearate, Sucrose Hexapalmitate, Sucrose Laurate, Sucrose Mortierellate, Sucrose Myristate, Sucrose Octaacetate, Sucrose Oleate, Sucrose Palmitate, Sucrose Pentaerucate, Sucrose Polybehenate, Sucrose Polycottonseedate, Sucrose Polylaurate, Sucrose Polylinoleate, Sucrose Polyoleate, Sucrose Polypalmate, Sucrose Polysoyate, Sucrose Polystearate, Sucrose Ricinoleate, Sucrose Stearate, Sucrose Tetraisostearate, Sucrose Tetrastearate Triacetate, Sucrose Tribehenate, and Sucrose Tristearate.

m. Alkyl Sulfoxides

Fatty amphiphiles of the present invention further may be selected from alkyl sulfoxide compounds according to the following formula:

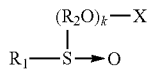

wherein R$_1$ is as described above; R$_2$ is a C$_1$-C$_5$ carbon chain which can be branched or hydroxy substituted; k is a number ranging from about 0 to about 10; and X and Y each is independently selected from hydrogen or a C$_1$-C$_4$ carbon chain which can be branched or hydroxy substituted.

Non-limiting examples of suitable alkyl sulfoxide compounds include octadecyl methyl sulfoxide, 2-ketotridecyl methyl sulfoxide, 3,6,9,-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, and 3-hydroxy-4-dodecoxybutyl methyl sulfoxide.

2. Secondary Surfactant

The gel network component of the present invention also comprises a secondary surfactant. As used herein, "secondary surfactant" refers to one or more surfactants which are combined with the fatty amphiphile and water to form the gel network of the present invention as a pre-mix separate from the other components of the shampoo composition. The secondary surfactant is separate from and in addition to the detersive surfactant component of the shampoo composition. However, the secondary surfactant may be the same or different type of surfactant or surfactants as that or those selected for the detersive surfactant component described above.

The shampoo compositions of the present invention comprise secondary surfactant as part of the pre-formed dispersed gel network phase in an amount from about 0.01% to about 15%, preferably from about 0.1% to about 10%, and more preferably from about 0.3% to about 5%, by weight of the shampoo composition.

As described above, for use in the present invention, the weight ratio of the fatty amphiphile to the secondary surfactant is greater than about 1:9, preferably greater than about 1:5 to about 100:1, more preferably greater than about 1:1 to about 50:1, and even more preferably greater than about 2:1 to about 10:1.

Suitable secondary surfactants include anionic, zwitterionic, amphoteric, cationic, and nonionic surfactants as generally described above in the Detersive Surfactant section.

Preferred anionic surfactants for use as secondary surfactants of the present invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and combinations thereof.

Cationic surfactants suitable for use as secondary surfactants of the present invention include quaternary ammonium salts or amido-amines having at least one fatty chain containing at least about 8 carbon atoms and mixture thereof.

Suitable quaternary ammonium salts have the following general formula:

wherein $R_1$ is selected from linear and branched radicals comprising from about 8 to about 12 carbon atoms; $R_2$ is selected from linear and branched radicals comprising from about 8 to 12 carbon atoms or the same group as radicals $R_3$ and $R_4$; $R_3$ and $R_4$ are independently selected from linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy, and alkylamide radicals; and X— is an anion selected from halides such as chloride, bromide, and iodide, ($C_2$-$C_6$) alkyl sulphates, such as methyl sulphate, phosphates, alkyl, and alkylaryl sulphonates, and anions derived from organic acids, such as acetate and lactate.

Non-limiting examples of such suitable cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, and mixtures thereof.

Suitable amido-amine cationic surfactants have the following general formula:

wherein $R'_1$ is selected from linear and branched radicals comprising about 8 to about 12 carbon atoms; $R'_2$ and $R'_3$ are independently selected from hydrogen, linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy and alkylamide radicals; and n is an integer from about 1 to about 4.

Non-limiting examples of such suitable amido-amines include stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Suitable nonionic surfactants include nonionic surfactants having an HLB of 7 or more and comprising one or more polyethyleneoxide chains wherein each polyethyleneoxide chain contains on average at least about 5 ethylene oxide units.

Nonionic surfactants comprising one or more polyethyleneoxide chain wherein each polyethyleneoxide chain contains on average at least about 5 ethylene oxide units include polyoxyethylene alkyl ethers, polyethyleneglycol fatty acid esters, polyoxyethylene castor oil, polyoxyethylene hydrogenated castor oil, polyoxyethylene fatty amides and their monoethanolamine and diethanolamine derivatives, and polyethoxylated fatty amines, with a number of ethylene oxide groups of at least about 5, and mixtures thereof.

Among preferred nonionic surfactants comprising one or more polyethyleneoxide chain include polyoxyethylene alkyl ethers having at least about 5, preferably from about 10 to 20, ethylene oxide units. Examples of such nonionic surfactants are steareth-10 and steareth-15.

Also suitable for use as nonionic surfactants are nonionic surfactants having an HLB of 7 or more which are free of polyethyleneoxide chains. Nonionic surfactants free of polyethyleneoxide chains include polyglycerolated fatty acids, polyglycerolated fatty amides, polyglycerolated alkyl phenols, polyglycerolated α-diols, polyglycerolated alcohols, alkyl polyglucosides, and sugar esters. Preferably, suitable nonionic surfactants free of polyethyleneoxide chains are selected from alkyl polyglucosides, sugar esters, polyglyceryl fatty acid esters, alkyl polyglyceryl ethers, and mixtures thereof.

Suitable secondary surfactants of the present invention also include so-called gemini surfactants. Gemini surfactants are generally described by F. M. Menger and C. A. Littau, "Gemini Surfactants: A New Class of Self-Assembling Molecules", *J. Am. Chem. Soc.* 1993, 115, 10083-10090; and by B. S. Sekon, "Gemini (dimeric) Surfactants: The Two Faced Molecules", *Resonance,* 42-49 (March 2004). Examples of suitable gemini surfactants are described in U.S. Pat. Nos. 5,922,671; 6,204,297; 6,358,914; 6,710,022; 6,777,384; 6,794,345; and 6,797,687.

More than one surfactant of the above specified types may be used for the secondary surfactant of the present invention.

3. Water or Suitable Solvents

The gel network component of the present invention also comprises water or suitable solvents. The water or suitable solvent and the secondary surfactant together contribute to the swelling of the fatty amphiphile. This, in turn, leads to the formation and the stability of the gel network. As used herein, the term "suitable solvent" refers to any solvent which can be used in the place of or in combination with water in the formation of the gel network of the present invention.

The shampoo compositions of the present invention comprise water or suitable solvents as part of the pre-formed dispersed gel network phase in an amount suitable to achieve a gel network when combined with fatty amphiphile and secondary surfactant according to the present invention.

In a preferred embodiment, the shampoo compositions of the present invention comprise as part of the pre-formed dispersed gel network phase at least about 0.05% of water or a suitable solvent, by weight of the shampoo composition.

In another embodiment of the present invention, the shampoo compositions comprise water or a suitable solvent as part of the pre-formed dispersed gel network phase is an amount relative to the amount of fatty amphiphile at a weight ratio of at least about 1:1.

C. Aqueous Carrier

The shampoo compositions of the present invention comprise an aqueous carrier. Typically, the compositions of the present invention are in the form of pourable liquids (under ambient conditions). The compositions, therefore, comprise an aqueous carrier at a level of from about 20% to about 95%, preferably from about 60% to about 85%, by weight of the compositions. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

D. Additional Components

The compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

1. Deposition Aid

The shampoo compositions of the present invention may include a deposition aid. The deposition aid is included to effectively enhance deposition of the gel network component. The deposition aid can comprise any material that enhances the deposition of the gel network from the shampoo onto the hair and/or scalp.

The concentration of the deposition aid in the shampoo composition should be sufficient to effectively enhance the deposition of the gel network component and ranges from about 0.05% to about 5%, preferably from about 0.075% to about 2.5%, more preferably from about 0.1% to about 1.0%, by weight of the shampoo composition.

In one embodiment of the present invention, the deposition aid is a cationic polymer. Preferred cationic polymers will have cationic charge densities of at least about 0.4 meq/g, preferably at least about 1.2 meq/g, more preferably at least about 1.5 meq/g, but also preferably less than about 7 meq/g, more preferably less than about 5 meq/g, at the pH of intended use of the composition. The pH will generally range from about pH 3 to about pH 9, preferably between about pH 4 and about pH 8. The "cationic charge density" of a polymer, as that term is used herein, refers to the ratio of the number of positive charges on the polymer to the molecular weight of the polymer. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non-limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. These preferred monomers conform the to the formula

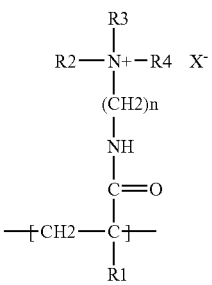

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A. Also preferred are copolymers of the above cationic monomer with nonionic monomers such that the charge density of the total copolymer is from about 2.0 meq/g to about 4.5 meq/g.

Other suitable cationic polymers for use in the composition include polysaccharide polymers, such as cationic cellulose derivatives and cationic starch derivatives. Suitable cationic polysaccharide polymers include those which conform to the formula

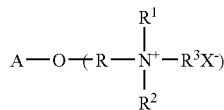

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially avaialable from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

2. Dispersed Particles

The composition of the present invention may include dispersed particles. Particles useful in the present invention can be inorganic, synthetic, or semi-synthetic in origin. If present in the compositions of the present invention, dispersed particles are incorporated in an amount from about 0.025% to about 20%, preferably from about 0.05% to about 10%, more preferably from about 0.1% to about 5%, even more preferably from about 0.25% to about 3%, and yet more preferably from about 0.5% to about 2%, by weight of the composition.

3. Nonionic Polymers

Polyalkylene glycols having a molecular weight of more than about 1000 are useful herein. Useful are those having the following general formula:

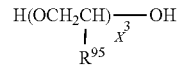

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

4. Conditioning Agents

The compositions of the present invention may also comprise one or more conditioning agents. Conditioning agents include materials which are used to give a particular conditioning benefit to hair and/or skin. The conditioning agents useful in the compositions of the present invention typically comprise a water-insoluble, water-dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

One or more conditioning agents are present from about 0.01% to about 10%, preferably from about 0.1% to about 8%, more preferably from about 0.2% to about 4%, by weight of the composition.

The conditioning agents may be present in the dispersed gel network phase or may be added to the final shampoo composition as a separate component.

a. Silicones

The conditioning agents of the compositions of the present invention may be a water-insoluble silicone conditioning agent. The silicone conditioning agent may comprise volatile silicone, non-volatile silicone, or combinations thereof. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. Nos. 5,104,646, and 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 10,000 to about 1,500,000 csk, more preferably from about 20,000 to about 1,000,000 csk.

In an opaque composition embodiment of the present invention, the personal care composition comprises a non-volatile silicone oil having a particle size as measured in the personal care composition from about 1 μm to about 50 μm. In an embodiment of the present invention for small particle application to the hair, the personal care composition comprises a non-volatile silicone oil having a particle size as measured in the personal care composition from about 100 nm to about 1 μm. A substantially clear composition embodiment of the present invention comprises a non-volatile silicone oil having a particle size as measured in the personal care composition of less than about 100 nm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the compositions of the present invention are disclosed in U.S. Pat. Nos. 2,826,551, 3,964,500, 4,364,837, British Pat. No. 849,433, and *Silicon Compounds*, Petrarch Systems, Inc. (1984).

i. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (I):

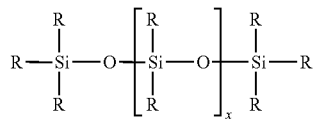

wherein R is aliphatic, preferably alkyl or alkenyl, or aryl, R can be substituted or unsubstituted, and x is an integer from 1 to about 8,000. Suitable R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri- alkylamino and alkoxyamino groups, wherein the aliphatic portion chain length is preferably as described herein.

ii. Amino and Cationic Silicones

Amino and/or cationic silicone fluids suitable for use in the compositions of the present invention include, but are not limited to, those which conform to the general formula (II):

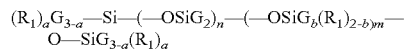

wherein G is hydrogen, phenyl, hydroxy, or $C_1$-$C_8$ alkyl, preferably methyl; a is 0 or an integer having a value from 1 to 3, preferably 0; b is 0 or 1, preferably 1; n is a number from 0 to 1,999, preferably from 49 to 499; m is an integer from 1 to 2,000, preferably from 1 to 10; the sum of n and m is a number from 1 to 2,000, preferably from 50 to 500;

$R_1$ is a monovalent radical conforming to the general formula $C_qH_{2q}L$, wherein q is an integer having a value from 2 to 8 and L is selected from the following groups:

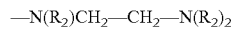

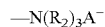

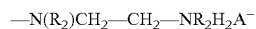

wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred amino silicone corresponding to formula (II) is the polymer known as "trimethylsilylamodimethicone", which is shown below in formula (III):

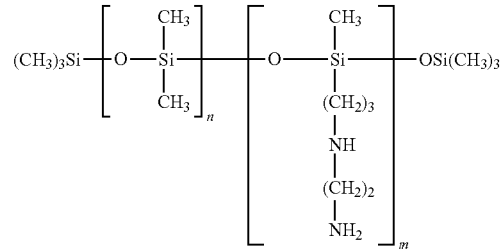

Other silicone cationic polymers which may be used in the compositions of the present invention are represented by the general formula (IV):

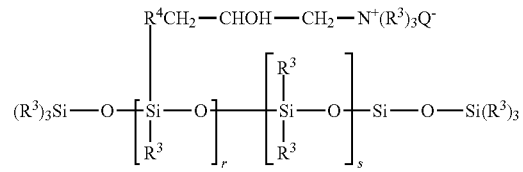

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

iii. Silicone Gums

Other silicone fluids suitable for use in the compositions of the present invention are the water-insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

iv. High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (I) above, as well as cyclic polysiloxanes such as those represented by Formula (V) below:

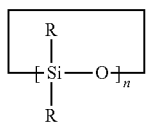

wherein R is as defined above for Formula (I), and n is a number from about 3 to about 7, preferably from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, preferably at least about 20%, more preferably at least about 25%, even more preferably at least about 35%, more preferably at least about 50%. Typically, the degree of aryl substitution will be less than about 90%, more generally less than about 85%, preferably from about 55% to about 80%.

Preferred high refractive index polysiloxane fluids have a combination of phenyl or phenyl derivative substituents (more preferably phenyl), with alkyl substituents, preferably $C_1$-$C_4$ alkyl (more preferably methyl), hydroxy, or $C_1$-$C_4$ alkylamino (especially —$R^1NHR^2NH_2$ wherein each $R^1$ and $R^2$ independently is a $C_1$-$C_3$ alkyl, alkenyl, and/or alkoxy).

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. Nos. 2,826,551, 3,964,500, 4,364,837, British Pat. No. 849,433, and *Silicon Compounds*, Petrarch Systems, Inc. (1984).

v. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

b. Organic Conditioning Oils

The conditioning component of the compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones described above.

i. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and, unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

ii. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

iii. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g., monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: iso-propyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate. Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (VI):

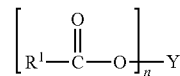

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (VII):

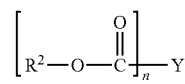

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (VII).

Specific non-limiting examples of suitable synthetic fatty esters for use in the compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

c. Other Conditioning Agents

Also suitable for use in the compositions herein are the conditioning agents described in U.S. Pat. Nos. 5,674,478; 5,750,122; 4,529,586; 4,507,280; 4,663,158; 4,197,865; 4,217,914; 4,381,919; and 4,422,853.

5. Anti-Dandruff Actives

The compositions of the present invention may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

Pyridinethione anti-microbial and anti-dandruff agents are described, for example, in U.S. Pat. Nos. 2,809,971; 3,236,733; 3,753,196; 3,761,418; 4,345,080; 4,323,683; 4,379,753; and 4,470,982. In an embodiment, the present invention may comprise pyrithione or a polyvalent metal salt of pyrithione. Any form of polyvalent metal pyrithione salts may be used, including platelet and needle structures. Preferred salts for use herein include those formed from the polyvalent metals magnesium, barium, bismuth, strontium, copper, zinc, cadmium, zirconium and mixtures thereof, more preferably zinc. Even more preferred for use herein is the zinc salt of 1-hydroxy-2-pyridinethione (known as "zinc pyrithione" or "ZPT"); more preferably ZPT in platelet particle form, wherein the particles have an average size of up to about 20 µm, preferably up to about 5 µm, more preferably up to about 2.5 µm. Such embodiments include from about 0.01% to about 5% of a pyrithione or polyvalent metal salt of a pyrithione; more preferably from about 0.1% to about 2%.

Azole anti-microbials include imidazoles such as climbazole and ketoconazole. Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition.

Selenium sulfide compounds are described, for example, in U.S. Pat. Nos. 2,694,668; 3,152,046; 4,089,945; and 4,885,107, all of which descriptions are incorporated herein by reference. Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm.

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

The present invention may further comprise one or more keratolytic agents such as salicylic acid.

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbazole combinations, and salicylic acid and octopirox combinations, and mixtures thereof.

In addition to the anti-microbial active selected from above, the present invention may comprise one or more antifungal or anti-microbial actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Preferred anti-microbials include itraconazole, ketoconazole, selenium sulphide and coal tar.

When present in the composition, the anti-dandruff active is included in an amount from about 0.01% to about 5%, preferably from about 0.1% to about 3%, and more preferably from about 0.3% to about 2%, by weight of the composition.

6. Humectants

The compositions of the present invention may contain a humectant. The humectants herein are selected from the group consisting of polyhydric alcohols, water soluble alkoxylated nonionic polymers, and mixtures thereof. The humectants, when used herein, are preferably present in an amount by weight of the composition from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

7. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%, by weight of the composition.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the preferred materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

8. Other Optional Components

The compositions of the present invention may contain other optional components. Optional components may be present in the dispersed gel network phase or may be added to the final shampoo composition as separate components.

For example, the compositions of the present invention may contain water-soluble and water-insoluble vitamins such as vitamins BI, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts. The compositions of present invention may further comprise materials useful for hair loss prevention and hair growth stimulants or agents.

The compositions of the present invention also may comprise materials selected from the group consisting of sugar amines (e.g., N-acetylglucosamine), vitamin B3 compounds, sodium dehydroacetate, dehydroacetic acid and its salts, phytosterols, soy derivatives (e.g., equol and other isoflavones), niacinamide, phytantriol, farnesol, bisabolol, salicylic acid compounds, hexamidines, dialkanoyl hydroxyproline compounds, flavonoids, N-acyl amino acid compounds, retinoids (e.g., retinyl propionate), water-soluble vitamins, ascorbates (e.g., vitamin C, ascorbic acid, ascorbyl glucoside, ascorbyl palmitate, magnesium ascorbyl phosphate, sodium ascorbyl phosphate), sunscreen actives, anti-cellulite agents, butylated hydroxytoluene, butylated hydroxyanisole, their derivatives, and combinations thereof.

Any other suitable optional component can also be included in the composition of the present invention, such as those ingredients that are conventionally used in given product types. The CTFA Cosmetic Ingredient Handbook, Tenth Edition (2004), published by the Cosmetic, Toiletry, and Fragrance Association, Inc., Washington, D.C., describes a wide variety of nonlimiting materials that can be added to the composition herein. Examples of these ingredient classes include, but are not limited to: abrasives, absorbents, aesthetic components such as perfumes and fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g., hydroquinone, kojic acid, ascorbic acid, magnesiuim ascorbyl phosphate, ascorbyl glucoside, pyridoxine), enzymes, coenzymes, skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), thickeners (including a mono- or divalent salt such as sodium chloride), and vitamins, their derivatives, and combinations thereof.

E. Process of Making a Shampoo Composition

An aspect of the invention relates to a process of making a shampoo composition of the present invention. The process of making a shampoo composition comprises (a) combining a fatty amphiphile, a secondary surfactant, and water at a temperature sufficient to allow partitioning of the secondary surfactant and the water into the fatty amphiphile to form a pre-mix; (b) cooling the pre-mix below the chain melt temperature of the fatty amphiphile to form a gel.network; (c) adding the gel network to one or more detersive surfactants and an aqueous carrier to form a shampoo composition.

As discussed above, in one embodiment of the present invention, the gel network component is prepared as a separate pre-mix, which, after being cooled, is subsequently incorporated with the other components of the shampoo composition. More specifically, the gel network component of the present invention may be prepared by heating the fatty amphiphile, the secondary surfactant, and water to a level in the range of about 75° C. to about 90° C. and mixing. This mixture is cooled to a level in the range of about 27° C. to about 35° C. by, for example, passing the mixture through a heat exchanger. As a result of this cooling step, the fatty amphiphile and the secondary surfactant crystallize to form a crystalline gel network.

Alternative methods of preparing the gel network component include sonication and/or milling of the fatty amphiphile, the secondary surfactant, and water, while these components are heated, to reduce the particle size of the melted fatty amphiphile phase. This results in an increase in surface area of the fatty amphiphile phase, which allows the secondary surfactant and the water to swell the fatty amphiphile phase. Another suitable variation in preparing the gel network includes heating and mixing the fatty amphiphile and the secondary surfactant first, and then adding that mixture to the water.

F. Method of Use

The compositions of the present invention are used in a conventional manner for cleansing and conditioning hair or skin, including scalp, face, and body. Generally, a method of treating hair or skin of the present invention comprises applying the composition of the present invention to the hair or skin. More specifically, an effective amount of the personal care composition is applied to the hair or skin, which has preferably been wetted with water, and then the personal care composition is rinsed off. Such effective amounts generally range from about 1 g to about 50 g, preferably from about 1 g to about 20 g. Application to the hair typically includes working the composition through the hair such that most or all of the hair is contacted with the composition.

The method for treating the hair or skin comprises the steps of: (a) wetting the hair or skin with water; (b) applying an effective amount of the shampoo composition to the hair or skin, and (c) rinsing the applied areas of skin or hair with water. These steps can be repeated as many times as desired to achieve the desired cleansing and conditioning benefit.

In one embodiment, the shampoo composition of the present invention advantageously is used to treat damaged hair. Damaged hair may include hair selected from permed hair, oxidatively colored hair, and mechanically damaged hair.

In another embodiment, the shampoo composition is used to treat skin, such as the scalp, the face, and the body.

The personal care compositions of this invention may be used as liquids, solids, semi-solids, flakes, gels, placed in a pressurized container with a propellant added, or used in a pump spray form. The viscosity of the product may be selected to accommodate the form desired.

NON-LIMITING EXAMPLES

The shampoo compositions illustrated in the following Examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced conditioning benefits to the hair.

The shampoo compositions illustrated in the following Examples are prepared by conventional formulation and mixing methods, an example of which is set forth hereinbelow. All exemplified amounts are listed as weight percents on an active basis and exclude minor materials such as diluents, preservatives, color solutions, imagery ingredients, botanicals, and so forth, unless otherwise specified. All percentages are based on weight unless otherwise specified.

Preparation of the Gel Network Pre-Mix

To prepare the gel network pre-mix, about 20% of the water is heated to about 74° C. and the fatty amphiphile and the secondary surfactant (e.g., Behenyltrimethylammonium chloride (Varisoft BT-85) or Sodium Laureth Sulfate) are added to it. After incorporation, this mixture is passed through a mill and heat exchanger where it is cooled to about 35° C. As a result of this cooling step, the fatty amphiphile, the secondary surfactant, and the water form a crystalline gel network.

For mixtures of different fatty amphiphiles, it may be beneficial to pre-mix the fatty amphiphile materials before incorporation into the water. This can be done by co-melting the different fatty amphiphiles together and utilizing this melt or cooling into a solid phase and incorporating this into the heated water along with the secondary surfactant. Another variation could be to co-melt the one or more fatty amphiphiles and the secondary surfactant before incorporation into the water. Some gel network compositions with chain melt temperatures between about 27° C. to about 35° C. will need to be cooled below 27° C. to ensure the lamellar phase structure is froze.

Gel Network Pre-Mix Examples 1-77

The following Examples illustrate specific embodiments of the gel network pre-mix, prior to its incorporation with the detersive surfactant and other components of the final shampoo composition of the present invention. It is intended that each of the following gel network pre-mix examples could be incorporated as a dispersed phase into a shampoo composition according to the present invention.

| Ingredient | 1 | 2 | 3 | 4 | 5 | 6 | 7 |
|---|---|---|---|---|---|---|---|
| Water | 88.55% | 88.55% | 88.55% | 88.55% | 88.55% | 88.55% | 88.55% |
| Behenamidopropyl dimethylamine, Incromine BB (2) | 8.58% | | | | | | |
| Glyceryl distearate (1) | | 8.58% | | | | | |
| Glyceryl hydroxystearate (1) | | | 8.58% | | | | |
| Glyceryl palmitate (1) | | | | 8.58% | | | |
| Glyceryl stearate, Glyceryl Stearate Pure (1) | | | | | 8.58% | | |
| Oleamide, Croadmide VRX Bead (2) | | | | | | 8.58% | |
| Palmitic acid (3) | | | | | | | 8.58% |
| Behenyltrimethylammonium chloride, Varisoft BT-85(4) | 2.84% | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% | 0.03% |

| Ingredient | 8 | 9 | 10 | 11 | 12 | 13 | 14 |
|---|---|---|---|---|---|---|---|
| Water | 88.55% | 88.55% | 88.55% | 88.55% | 88.55% | 88.55% | 88.55% |
| PEG-2 Stearate (1) | 8.58% | | | | | | |
| PEG-5 Glyceryl stearate (1) | | 8.58% | | | | | |
| PEG-6 Stearate (1) | | | 8.58% | | | | |
| SEFA Stearate, Sefose-1618H (3) | | | | 8.58% | | | |
| Sorbitan palmitate (1) | | | | | 8.58% | | |
| Sorbitan stearate, Crill 3 NF (2) | | | | | | 8.58% | |
| Sorbitan stearate (1) | | | | | | | 8.58% |
| Behenyltrimethylammonium chloride, Varisoft BT-85(4) | 2.84% | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% | 0.03% |

| Ingredient | 15 | 16 | 17 | 18 | 19 | 20 | 21 |
|---|---|---|---|---|---|---|---|
| Water | 88.55% | 88.55% | 88.55% | 88.55% | 88.55% | 88.55% | 88.55% |
| Glyceryl palmitate (1) | | | | | | 4.29% | |
| Glyceryl stearate, Glyceryl Stearate Pure (1) | | | | | | 4.29% | |
| Sorbitan tristearate (1) | 8.58% | | | | | | |
| Stearamide MEA-stearate (1) | | 8.58% | | | | | |
| Steareth-2, Volpo S-2 (2) | | | 8.58% | | | | 6.44% |
| Stearic acid, V-1890 (3) | | | | 8.58% | | | 2.14% |
| Sucrose distearate, Crodesta F-10 (2) | | | | | 8.58% | | |
| Behenyltrimethylammonium chloride, Varisoft BT-85 (4) | 2.84% | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% | 0.03% |

| Ingredient | 22 | 23 | 24 | 25 | 26 | 27 | 28 |
|---|---|---|---|---|---|---|---|
| Water | 82.75% | 82.75% | 82.75% | 82.75% | 82.75% | 82.75% | 82.75% |
| Behenamidopropyl dimethylamine, Incromine BB (2) | 8.58% | | | | | | |
| Glyceryl distearate (1) | | 8.58% | | | | | |
| Glyceryl hydroxystearate (1) | | | 8.58% | | | | |
| Glyceryl palmitate (1) | | | | 8.58% | | | |
| Glyceryl stearate, Glyceryl Stearate Pure (1) | | | | | 8.58% | | |
| Oleamide, Crodamide VRX Bead (2) | | | | | | 8.58% | |
| Palmitic acid, V-1695 (3) | | | | | | | 8.58% |
| Sodium laureth-3 sulfate (28% Active) | 8.64% | 8.64% | 8.64% | 8.64% | 8.64% | 8.64% | 8.64% |
| 5-Chloro-2-methyl-4-isothiazolin-3-one, Kathon CG | 0.03% | 0.03% | 0.03% | 0.03% | 0.03% | 0.03% | 0.03% |

| Ingredient | 29 | 30 | 31 | 32 | 33 | 34 | 35 |
|---|---|---|---|---|---|---|---|
| Water | 82.75% | 82.75% | 82.75% | 82.75% | 82.75% | 82.75% | 82.75% |
| PEG-2 Stearate (1) | 8.58% | | | | | | |
| PEG-5 Glyceryl stearate (1) | | 8.58% | | | | | |
| PEG-6 Stearate (1) | | | 8.58% | | | | |
| SEFA Stearate, Sefose-1618H (3) | | | | 8.58% | | | |
| Sorbitan palmitate (1) | | | | | 8.58% | | |
| Sorbitan stearate, Crill 3 NF (2) | | | | | | 8.58% | |
| Sorbitan stearate (1) | | | | | | | 8.58% |
| Sodium laureth-3 sulfate (28% Active) | 8.64% | 8.64% | 8.64% | 8.64% | 8.64% | 8.64% | 8.64% |
| 5-Chloro-2-methyl-4-isothiazolin-3-one, Kathon CG | 0.03% | 0.03% | 0.03% | 0.03% | 0.03% | 0.03% | 0.03% |

-continued

| Ingredient | 36 | 37 | 38 | 39 | 40 | 41 | 42 |
|---|---|---|---|---|---|---|---|
| Water | 82.75% | 82.75% | 82.75% | 86.14% | 82.75% | 82.75% | 82.75% |
| Cetyl Alcohol | | | | 3.46% | | | |
| Cocamine oxide | | | | | | | 4.30% |
| Glyceryl distearate (1) | | | | | | 4.30% | |
| Sorbitan tristearate (1) | 8.58% | | | | | | |
| Steary Alcohol | | | | 6.44% | | | |
| Stearamide MEA-stearate (1) | | 8.58% | | | | | |
| Steareth-2, Volpa S-2 (2) | | | 8.58% | | | | |
| Stearic acid, V-1890 (3) | | | | | | 4.28% | |
| Sucrose distearate, Crodesta F-10 (2) | | | | | 8.58% | | 4.28% |
| Sodium laureth-3 sulfate (28% Active) | 8.64% | 8.64% | 8.64% | 3.93% | 8.64% | 8.64% | 8.64% |
| 5-Chloro-2-methyl-4-isothiazolin-3-one, Kathon CG | 0.03% | 0.03% | 0.03% | 0.03% | 0.03% | 0.03% | 0.03% |

| Ingredient | 43 | 44 | 45 | 46 | 47 | 48 | 49 |
|---|---|---|---|---|---|---|---|
| Water | 88.78% | 88.78% | 88.78% | 88.78% | 88.78% | 88.78% | 88.78% |
| Behenamidopropyl dimethylamine, Incromine BB (2) | 9.90% | | | | | | |
| Glyceryl distearate (1) | | 9.90% | | | | | |
| Glyceryl hydroxystearate (1) | | | 9.90% | | | | |
| Glyceryl stearate, Glyceryl Stearate Pure (1) | | | | 9.90% | | | |
| PEG-2 Stearate (1) | | | | | 9.90% | | |
| PEG-6 Stearate (1) | | | | | | 9.90% | |
| Sorbitan stearate, Crill 3 NF (2) | | | | | | | 9.90% |
| Behenyltrimethylammonium chloride, Varisoft BT-85 (2) | 1.29% | 1.29% | 1.29% | 1.29% | 1.29% | 1.29% | 1.29% |
| 5-Chloro-2-methyl-4-isothiazolin-3-one, Kathon CG | 0.03% | 0.03% | 0.03% | 0.03% | 0.03% | 0.03% | 0.03% |

| Ingredient | 50 | 51 | 52 | 53 | 54 | 55 | 56 |
|---|---|---|---|---|---|---|---|
| Water | 88.78% | 88.55% | 88.78% | 88.78% | 88.78% | 88.78% | 88.78% |
| Glyceryl distearate (1) | | | | 4.95% | | | |
| Stearyl Alcohol | | 5.57% | | | | 2.48% | 3.21% |
| Cetyl Alcohol | | 3.00% | | | | 2.47% | 1.74% |
| Glyceryl hydroxystearate (1) | | | | | 4.95% | | |
| PEG-2 Stearate (1) | | | | | 4.95% | | |
| Stearamide MEA-stearate (1) | 9.90% | | | | | | |
| Steareth-2, Volpo S-2 (2) | | | 4.95% | | 4.95% | | |
| Stearic acid, V-1890 (3) | | | 4.95% | 4.95% | 4.95% | 4.95% | 4.95% |
| Behenyltrimethylammonium chloride, Varisoft BT-85 (2) | 1.29% | 2.85% | 1.29% | 1.29% | 1.29% | 1.29% | 1.29% |
| 5-Chloro-2-methyl-4-isothiazolin-3-one, Kathon CG | 0.03% | 0.03% | 0.03% | 0.03% | 0.03% | 0.03% | 0.03% |

| Ingredient | 57 | 58 | 59 | 60 | 61 | 62 | 63 |
|---|---|---|---|---|---|---|---|
| Water | 86.14% | 86.14% | 86.14% | 86.14% | 86.14% | 86.14% | 86.14% |
| Glyceryl distearate (1) | 9.90% | | | | | 4.950% | |
| Glyceryl stearate, Glyceryl Stearate Pure (1) | | 9.90% | | | | | 4.950% |
| PEG-2 Stearate (1) | | | 9.90% | | | 4.950% | |
| Steareth-2, Volpo S-2 (2) | | | | 9.90% | 4.95% | | |
| Stearic acid, V-1890 (3) | | | | | 4.95% | | 4.95% |
| Sodium laureth-3 sulfate (28% Active) | 3.93% | 3.93% | 3.93% | 3.93% | 3.93% | 3.93% | 3.93% |
| 5-Chloro-2-methyl-4-isothiazolin-3-one, Kathon CG | 0.03% | 0.03% | 0.03% | 0.03% | 0.03% | 0.03% | 0.03% |

| Ingredient | 64 | 65 | 66 | 67 | 68 | 69 | 70 |
|---|---|---|---|---|---|---|---|
| Water | 87.13% | 82.13% | 77.13% | 72.13% | 67.13% | 77.13% | 77.13% |
| Cetyl Alcohol | 3.50% | 5.25% | 7.00% | 8.75% | 10.50% | 7.00% | 7.00% |
| Glyceryl palmitate (1) | | | | | | | 6.50% |
| Oleyl Alcohol | | | | | | 1.00% | |
| Sorbitan stearate (1) | | | | | | 6.50% | |
| Stearyl Alcohol | 6.50% | 9.75% | 13.00% | 16.25% | 19.50% | 5.50% | 6.50% |
| Behenyltrimethylammonium chloride, Varisoft BT-85 (4) | 2.84% | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% | 0.03% |

| Ingredient | 71 | 72 | 73 | 74 | 75 | 76 | 77 |
|---|---|---|---|---|---|---|---|
| Water | 86.14% | 82.75% | 72.60% | 72.60% | 72.60% | 82.75% | 80.43% |
| Behenyl Alcohol | | | | | 7.87% | | 7.87% |
| Cetyl Alcohol | 3.46% | 4.18% | 5.62% | | | | |
| Glyceryl distearate (1) | | | | | | 4.30% | |
| Steary Alcohol | 6.44% | 7.52% | 10.12% | | 7.87% | | 7.87% |
| Steareth-2, Volpa S-2 (2) | | | | 5.62% | | | |
| Stearic acid, V-1890 (3) | | | | 10.12% | | | |
| Sodium laureth-3 sulfate (28% Active) | 3.93% | 4.64% | 11.63% | | 11.63% | 8.64% | |
| Behenyltrimethylammonium chloride, Varisoft BT-85 (4) | | | | 3.83% | | | 3.83% |
| 5-Chloro-2-methyl-4-isothiazolin-3-one, Kathon CG | 0.03% | 0.03% | 0.03% | 0.03% | 0.03% | 0.03% | 0.03% |

(1) available from A&E Connock
(2) available from Croda Chemicals
(3) available from P&G Chemicals
(4) available Goldschmidt Chemical

Preparation of Final Shampoo Compositions

To prepare the final shampoo composition, first, a surfactant solution pre-mix is formed. To prepare this surfactant solution pre-mix, about 6% to about 9% of sodium or ammonium laureth-3 sulfate, cationic polymers, and about 0% to about 5% of water are added to a jacketed mix tank and heated to about 74° C. with agitation. To this solution, citric acid, sodium citrate, sodium benzoate, and disodium EDTA are added to the tank and allowed to disperse. Ethylene glycol distearate (EGDS) is then added to the mixing vessel and melted. After the EGDS is well dispersed (e.g., after about 10 minutes), preservative is added and mixed into the surfactant solution. This mixture is passed through a mill and heat exchanger where it is cooled to about 35° C. and collected in a finishing tank. As a result of this cooling step, the EGDS crystallizes to form a waxy crystalline suspension. The mixture of these components is the surfactant solution pre-mix.

Next, the surfactant solution pre-mix and the gel network pre-mix, which is prepared as described above, are mixed together. The remainder of the surfactants, perfume, dimethicone, sodium chloride or ammonium xylene sulfonate for viscosity adjustment, and other additional componenets when used, and the remainder of the water are added with ample agitation to ensure a homogeneous mixture. This mixture is the final shampoo composition which comprises as a dispersed phase the gel network pre-mix.

Preferred viscosities of the final shampoo composition according to the present invention range from about 5000 to about 15,000 centipoise at 27° C., as measured by a Wells-Brookfield model RVTDCP viscometer using a CP-41 cone and plate at 2/s at 3 minutes.

The pH may be adjusted as necessary to provide shampoo compositions of the present invention which are suitable for application to human hair, and may vary based on the selection of particular detersive surfactants, fatty amphiphiles, and/or other components.

Shampoo Examples 1-40

The following Examples illustrate specific embodiments of the final shampoo composition of the present invention, which respectively comprise select above-exemplified gel network pre-mixes as a dispersed phase.

| Ingredient | 1 | 2 | 3 | 4 | 5 | 6 | 7 | 8 | 9 | 10 |
|---|---|---|---|---|---|---|---|---|---|---|
| Sodium Laureth Sulfate | 10.00 | 10.00 | 10.00 | 10.00 | 10.00 | 10.00 | 10.00 | 10.00 | 10.00 | 7.65 |
| Sodium Lauryl Sulfate | 1.50 | 1.50 | 1.50 | 1.50 | 1.50 | 6.00 | 6.00 | 6.00 | 6.00 | 6.35 |
| Cocamidopropyl betaine | 2.00 | 2.00 | 2.00 | 3.00 | 3.00 | | | | | |
| Cocamide MEA | | | | | | | | | 0.60 | |
| Any one of Gel Networks 1–21 | 27.27 | 27.27 | 27.27 | | | 27.27 | 27.27 | 13.64 | 6.82 | 27.27 |
| Gel Network 39 | | | | | 27.27 | | | | | |
| Gel Network 51 | | | | 27.27 | | | | | | |
| Guar Hydroxypropyl trimonium chloride (1) | 0.40 | | | | | | | | | |
| Guar Hydroxypropyl trimonium chloride (2) | | 0.40 | | | | | | | | |
| Guar Hydroxypropyl trimonium chloride (3) | | | 0.40 | | | | | 0.20 | | 0.40 |
| Guar Hydroxypropyl trimonium chloride (4) | | | | | | | | | 0.20 | |
| Polyquaterium-10 (5) | | | | | | | 0.40 | | | |
| Polyquaterium-10 (6) | | | | | | 0.40 | | | | |

-continued

| Ingredient | | | | | | | | | | |
|---|---|---|---|---|---|---|---|---|---|---|
| Polyquaterium-10 (7) | | | | 0.40 | 0.40 | | | | | |
| PEG-7M (8) | | | | | | 0.10 | | | | |
| Dimethicone (9) | 2.00 | 2.00 | 2.00 | 2.00 | 2.00 | 2.00 | 2.00 | 2.00 | 2.00 | 2.00 |
| Ethylene Glycol Distearate | 1.50 | 1.50 | 1.50 | 1.50 | 1.50 | 1.50 | 1.50 | 1.50 | 1.50 | 1.50 |
| 5-Chloro-2-methyl-4-isothiazolin-3-one, Kathon CG | 0.0005 | 0.0005 | 0.0005 | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 | 0.25 | 0.25 | 0.25 |
| Disodium EDTA | 0.13 | 0.13 | 0.13 | 0.13 | 0.13 | 0.13 | 0.13 | 0.13 | 0.13 | 0.13 |
| Perfume | 0.70 | 0.70 | 0.70 | 0.70 | 0.70 | 0.70 | 0.70 | 0.70 | 0.70 | 0.70 |
| Citric Acid/Sodium Citrate Dihydrate | pH QS | pH QS | pH QS | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS | Visc. QS | Visc. QS | Visc. QS |
| Water | QS | QS | QS | QS | QS | QS | QS | QS | QS | QS |

| Ingredient | 11 | 12 | 13 | 14 | 15 | 16 | 17 | 18 | 19 | 20 |
|---|---|---|---|---|---|---|---|---|---|---|
| Sodium Laureth Sulfate | | | | 10.00 | 7.65 | 7.65 | 7.65 | | | 7.65 |
| Sodium Lauryl Sulfate | | | | 1.50 | 6.35 | 6.35 | 6.35 | | | 6.35 |
| Ammonium Laureth Sulfate | 10.00 | 6.00 | 12.00 | | | | | 12.00 | 10.00 | |
| Ammonium Lauryl Sulfate | 6.00 | 10.00 | 2.00 | | | | | 2.00 | 2.00 | |
| Sodium Lauroamphoacetate | | | 2.00 | | | | | 2.00 | 2.00 | |
| Cocamidopropyl betaine | | | | 2.00 | | | | | 2.00 | |
| Cocamide MEA | | | | | | | | 0.60 | | |
| Any one of Gel Networks 1–21 | 27.27 | 27.27 | 27.27 | 27.27 | | | | 27.27 | 27.27 | |
| Gel Networks 64–68 | | | | | 27.27 | 13.64 | 6.82 | | | 27.27 |
| Guar Hydroxypropyl trimonium chloride (3) | | | | | 0.40 | 0.40 | 0.40 | | | |
| Polyqaterium-10 (5) | | | | | | | | 0.40 | | |
| Polyquaterium-10 (6) | | | | | | | | | | 0.10 |
| Polyquaterium-10 (7) | | | | | | | | | 0.40 | |
| PEG-7M (8) | | | | | | | | | | |
| Dimethicone (9) | 2.00 | 2.00 | 2.00 | 2.00 | 2.00 | 2.00 | 2.00 | | | 2.00 |
| Dimethicone (10) | | | | | | | | 2.00 | 2.00 | |
| Ethylene Glycol Distearate | 1.50 | 1.50 | 1.50 | 1.50 | 1.50 | 1.50 | 1.50 | 1.50 | 1.50 | 1.50 |
| 5-Chloro-2-methyl-4-isothiazolin-3-one, Kathon CG | 0.0005 | 0.0005 | 0.0005 | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 | 0.25 | 0.25 | 0.25 |
| Disodium EDTA | 0.13 | 0.13 | 0.13 | 0.13 | 0.13 | 0.13 | 0.13 | 0.13 | 0.13 | 0.13 |
| Perfume | 0.70 | 0.70 | 0.70 | 0.70 | 0.70 | 0.70 | 0.70 | 0.70 | 0.70 | 0.70 |
| Citric Acid/Sodium Citrate Dihydrate | pH QS | pH QS | pH QS | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS | Visc. QS | Visc. QS | Visc. QS |
| Water | QS | QS | QS | QS | QS | QS | QS | QS | QS | QS |

| Ingredient | 21 | 22 | 23 | 24 | 25 | 26 | 27 | 28 | 29 | 30 |
|---|---|---|---|---|---|---|---|---|---|---|
| Sodium Laureth Sulfate | 10 | 10 | 10 | 10 | 10 | 10 | 10 | 7.65 | 7.65 | 10 |
| Sodium Lauryl Sulfate | 6 | 6 | 6 | 6 | 1.5 | 1.5 | 1.5 | 6.35 | 6.35 | 6 |
| Cocamidopropyl betaine | | | | | 2 | 2 | 2 | | | |
| Cocamide MEA | 1.6 | 1.6 | 1.6 | 1.6 | | | 1 | | | 1.6 |
| Cetyl alcohol | 0.6 | 0.6 | 0.6 | 0.6 | | | | | | |
| Laureth 4 | | | | | | 1 | | | | |
| Gel Network 71 | 13.64 | 13.64 | | | 27.27 | | | 27.27 | | |
| Gel Network 73 | | | | 15.79 | | 15.79 | | | | |
| Gel Network 75 | | | 15.79 | | | | 15.79 | | | |
| Gel Network 72 | | | | | | | | | 27.27 | |
| Gel Network 74 | | | | | | | | | | 6.82 |

-continued

| | | | | | | | | | | |
|---|---|---|---|---|---|---|---|---|---|---|
| Zinc Pyrithione | 1 | 1 | 1 | 1 | 1 | | | 1 | 2 | 0.5 |
| Guar Hydroxypropyl trimonium chloride (2) | 0.5 | | | | | | | | | 0.5 |
| Guar Hydroxypropyl trimonium chloride (3) | | 0.4 | 0.4 | 0.4 | 0.4 | 0.4 | 0.4 | 0.4 | | |
| Polyquaterium-10 (5) | | | 0.1 | | | | | | 0.25 | |
| Dimethicone (9) | 0.85 | 0.85 | 0.85 | 2 | 2 | 2 | 2 | 1 | | 2 |
| Dimethicone (10) | | | | | | | | | 1 | |
| Ethylene Glycol Distearate | 1.5 | 1.5 | 1.5 | 1.5 | 1.5 | 1.5 | 1.5 | 1.5 | 1.5 | 1.5 |
| 5-Chloro-2-methyl-4-isothiazolin-3-one, Kathon CG | 0.0006 | 0.0006 | 0.0006 | 0.0006 | 0.0006 | 0.0006 | 0.0006 | 0.0006 | 0.0006 | 0.0006 |
| Sodium Benzoate | 0.25 | 0.25 | 0.25 | 0.25 | 0.25 | 0.25 | 0.25 | 0.25 | 0.25 | 0.25 |
| Perfume | 0.4 | 0.4 | 0.4 | 0.4 | 0.4 | 0.4 | 0.4 | 0.4 | 0.4 | 0.4 |
| Benzyl alcohol | 0.0225 | 0.0225 | 0.0225 | 0.0225 | 0.0225 | 0.0225 | 0.0225 | 0.0225 | 0.0225 | 0.0225 |
| Hydrochloric acid/ Sodium Hydroxide | pH QS | pH QS | pH QS | pH QS | pH QS | pH QS | pH QS | pH QS | pH QS | pH QS |
| Copper sulfate Citric Acid/ Sodium Citrate Dihydrate | pH QS | pH QS | pH QS | pH QS | pH QS | pH QS | pH QS | pH QS | pH QS | pH QS |
| Sodium Chloride/ Sodium Xylene Sulfonate | Visc. QS | Visc. QS | Visc. QS | Visc. QS | Visc. QS | Visc. QS | Visc. QS | Visc. QS | Visc. QS | Visc. QS |
| Water | QS | QS | QS | QS | QS | QS | QS | QS | QS | QS |

| Ingredient | 31 | 32 | 33 | 34 | 35 | 36 | 37 | 38 | 39 | 40 |
|---|---|---|---|---|---|---|---|---|---|---|
| Sodium Laureth Sulfate | 10 | 10 | | 10 | | 10 | 10 | 10 | 7.65 | 7.65 |
| Sodium Lauryl Sulfate | 6 | 6 | | 6 | | 1.5 | 1.5 | 1.5 | 6.35 | 6.35 |
| Ammonium Laureth Sulfate | | | 10 | | 10 | | | | | |
| Ammonium Lauryl Sulfate | | | 6 | | 1.5 | | | | | |
| Sodium Lauroamphoacetate | | | | | | | 2 | | | |
| Cocamidopropyl betaine | | | | | 2 | | 2 | 2 | | |
| Cocamide MEA | 1.6 | 1.6 | 1.6 | 1.6 | | | 1 | 1 | 0.8 | |
| Cetyl alcohol | 0.6 | 0.6 | 0.6 | 0.6 | | | | | | |
| Laureth 4 | | | | | | | 1 | 1 | | 0.75 |
| Gel Network 71 | 13.64 | 13.64 | | | 27.27 | 27.27 | | | | |
| Gel Network 73 | | | | 15.79 | | | | | | |
| Gel Network 75 | | | 15.79 | | | | | | | |
| Gel Network 72 | | | | | | | | | 15.79 | |
| Gel Network 74 | | | | | | | | 15.79 | | |
| Gel Network 76 | | | | | | | | | | 27.27 |
| Gel Network 77 | | | | | | | 15.79 | | | |
| Zinc Pyrithione | 1 | 1 | 1 | | 1 | 1 | | | 1 | 2 |
| Ketoconazole | | 1 | | | | | | | | 0.5 |
| Climbazole | 1.5 | | | | | | | 1 | | |
| Elubiol | | | 0.25 | | | | | | | |
| Copper pyrithione | | | | 1 | | | | | 0.5 | |
| Guar Hydroxypropyl trimonium chloride (2) | 0.5 | | 0.5 | | | | | | | 0.5 |
| Guar Hydroxypropyl trimonium chloride (3) | | 0.4 | | 0.4 | | 0.4 | 0.4 | 0.4 | | |
| Polyquaterium-10 (6) | | | | | | | | 0.5 | 0.4 | |
| Polyquaterium-10 (5) | | | 0.1 | | | | | | | |
| Dimethicone (9) | 1.5 | 0.85 | 0.85 | 2 | 2 | 2 | 2 | | | 0.85 |
| Dimethicone (10) | | | | | | | | | 0.5 | |
| Ethylene Glycol Distearate | 1.5 | 1.5 | 1.5 | 1.5 | 1.5 | 1.5 | 1.5 | 1.5 | 1.5 | 1.5 |
| 5-Chloro-2-methyl-4-isothiazolin-3-one, Kathon CG | 0.0006 | 0.0006 | 0.0006 | 0.0006 | 0.0006 | 0.0006 | 0.0006 | 0.0006 | 0.0006 | 0.0006 |
| Sodium Benzoate | 0.25 | 0.25 | 0.25 | 0.25 | 0.25 | 0.25 | 0.25 | 0.25 | 0.25 | 0.25 |
| Perfume | 0.4 | 0.4 | 0.4 | 0.4 | 0.4 | 0.4 | 0.4 | 0.4 | 0.4 | 0.4 |
| Benzyl alcohol | 0.0225 | 0.0225 | 0.0225 | 0.0225 | 0.0225 | 0.0225 | 0.0225 | 0.0225 | 0.0225 | 0.0225 |
| Hydrochloric acid/ Sodium Hydroxide | pH QS | pH QS | pH QS | pH QS | pH QS | pH QS | pH QS | pH QS | pH QS | pH QS |

-continued

| | | | | | | | | | | |
|---|---|---|---|---|---|---|---|---|---|---|
| Copper sulfate | | | | | 0.1 | 1 | | 0.5 | | |
| Citric Acid/ Sodium Citrate Dihydrate | pH QS | pH QS | pH QS | pH QS | pH QS | pH QS | pH QS | pH QS | pH QS | pH QS |
| Sodium Chloride/ Sodium Xylene Sulfonate | Visc. QS | Visc. QS | Visc. QS | Visc. QS | Visc. QS | Visc. QS | Visc. QS | Visc. QS | Visc. QS | Visc. QS |
| Water | QS | QS | QS | QS | QS | QS | QS | QS | QS | QS |

(1) Jaguar C17 available from Rhodia
(2) N-Hance 3269 (with Mol. W. of ~500,000 and 0.8 meq/g) available from Aqulaon/Hercules
(3) ADPP-5043HMW (with Mol. W. of ~1,200,000 and Char.Den. of 2.0 meq/g) available from Aqualon/Hercules
(4) ADPP-5043 LMW (with Mol. W. of ~500,000 and Char.Den. of 2.0 meq/g) available from Aqulaon/Hercules
(5) Polymer JR30M available from Amerchol/Dow Chemical
(6) Polymer LR30M available from Amerchol/Dow Chemical
(7) Polymer KG30M available from Amerchol/Dow Chemical
(8) Peg-7M Available from Amerchol/Dow Chemical
(9) Viscasil 330M available from General Electric Silicones
(10) DC1664 available from Dow Corning Silicones The fatty amphiphile deposition of these products is measured by treating a switch of hair with 3 cycles (2 lather/rinse steps per cycle, 0.1 g shampoo per g hair on each lather/rinse step) with the shampoo. Four switches are treated with each shampoo. The switches are then extracted with solvent and the level of adsorbed fatty amphiphile measured by gas chromatographic-mass spectrophotometric analysis of the extracts.

Analytical Methods and Examples

The following provides example X-ray analysis data and example differential scanning calorimetry ("DSC") data for several of the above-exemplified compositions.

| | X-Ray Data (WAXD) Fatty Chain d-spacing** | X-Ray Data (SAXS) Lamellar d-spacing** | DSC Melt Temperature Transition for Gel Network* |
|---|---|---|---|
| Gel Network Example # 39 | 4.13 Å | 247 Å | 67° C. |
| Gel Network Example # 51 | 4.13 Å | 270 Å | 74° C. |
| Shampoo Example # 5 | 4.13 Å | 93 Å | 38° C. |
| Shampoo Example # 4 | 4.13 Å | 93 Å | 38° C. |

*See Differential Scanning Calorimetry method for sample preparation and analysis techniques.
**See X-Ray method for sample preparation and analysis techniques.

Differential Scanning Calorimetry Method

The chain melt temperature of the layer in the gel network comprising the one or more fatty amphiphiles (i.e., the melt transition temperature for the gel network) may be obtained using differential scanning calorimetry according to the following method. Utilizing a TA Instruments Q100 DSC, approximately 50 mg of the gel network pre-mix or the final shampoo composition containing the gel network is placed into a stainless steel high volume DSC pan. The sample, along with an empty reference pan is placed into the instrument. The samples are analyzed using the following conditions/temperature program: Nitrogen Purge, Equilibrate@5.00° C. until an isothermal is reach for 2.00 min. Ramp the temperature at a rate of 3.00° C./min to 90.00° C. Each sample is analyzed in duplicate. The resulting DSC data is analyzed using TA Instruments Universal Analysis Software.

The use of DSC to measure the melt transition temperature for gel networks is further described by T. de Vringer et al., *Colloid and Polymer Science*, vol. 265, 448-457 (1987); and H. M. Ribeiro et al., *Intl. J. of Cosmetic Science*, vol. 26, 47-59 (2004).

X-Ray Analysis Method

Small-angle x-ray scattering ("SAXS") as used to resolve periodic structures in mesophases is essentially an x-ray diffraction technique. It is used in conjunction with conventional wide-angle x-ray diffraction ("WXRD") to characterize aggregate structures such as micelles, gel networks, lamella, hexagonal and cubic liquid crystals. The different mesophases that show periodic structures can be characterized by the relative positions (d-spacing) of their reflections as derived from the Bragg equation ($d=\lambda/2 \sin \theta$) where d represents the interplanar spacing, $\lambda$ the radiation wavelength and $\theta$ the scattering (diffraction) angle.

The one dimensional lamella gel network phase is characterized by the ratio of the interplanar spacings $d_1/d_1$, $d_1/d_2$, $d_1/d_3$, $d_1/d4$, $d_1/d_5$ having the values 1:2:3:4:5 etc. in the SAXS region (long-range order) and one or two invariant reflection(s) in the WXRD region (short-range) centered around 3.5 and 4.5 Å over a broad halo background. Other mesophases (e.g. hexagonal or cubic) will have characteristically different d-spacing ratios.

WXRD data are collected in transmission mode on a Stoe STADI-P diffractometer equipped with an image plate position-sensitive detector. The specimen is positioned between two milar films in the sample holder and placed in the path of the x-ray beam. The IP detector has a solid angle of about 120° 2$\theta$ and records diffracted x-ray beams simultaneously. Data are collected and analyzed using the XPOW software.

SAXS data are collected on Rigaku rotating anode generator with a fine focus filament equipped with a HI-STAR 2-dimensional area detector from Bruker-AXS. The setup has an evacuated chamber, which houses the specimen, conjoined with an evacuated tube leading to the detector to reduce air scatter. The specimen sample holder consists of copper plates with small rectangular cavities to hold the fluid-like material and also allow the transmission of the x-ray beam. The openings to the cavities are sealed with kapton windows to provide leak-free environment under vacuum. The 2-D data are azimuthally integrated and reduced to intensity versus scattering vector (q) or its d equivalent by a combination of GADDS software and in-house software modules implementing known techniques on the Igor platform.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
   a) from about 5% to about 50% of one or more anionic detersive surfactants, by weight of said shampoo composition;
   b) from about 5% to about 40% by weight of the shampoo composition of a pre-formed solid crystalline gel network phase consisting of:
      i) from about 0.05% to about 14% of one or more fatty alcohols by weight of said shampoo composition;
      ii) from about 0.3% to about 5% by weight of said shampoo composition of one or more surfactants selected from the group consisting of anionic, cationic, and mixtures thereof; and
      iii) water;
      wherein the fatty alcohol and the surfactants are combined in a ratio of from 1:1 to 40:1; and
   c) from about 20% to about 95% of an aqueous carrier, by weight of said shampoo composition; and
   d) from about 0.01% to about 5% by weight of said shampoo composition of an anti-dandruff active.

2. A shampoo composition according to claim 1, further comprising a deposition aid.

3. A shampoo composition according to claim 2, wherein said deposition aid is a cationic polymer.

4. A shampoo composition according to claim 3, wherein said cationic polymer has a molecular weight from about 10,000 to about 10,000,000 and a charge density from about 0.9 meq/g to about 7.0 meq/g.

5. A shampoo composition according to claim 4, wherein said charge density is from about 0.9 meq/g to about 5 meq/g.

6. A shampoo composition according to claim 1, further comprising a suspending agent.

7. A shampoo composition according to claim 6, wherein said suspending agent is a crystalline suspending agent.

8. A shampoo composition according to claim 1, wherein the anti-dandruff active is selected from the group consisting of pyridinethione salts, azoles, selenium sulfide, particulate sulfur, keratolytic agents, octopirox, ciclopirox olamine, melaleuca, charcoal, and mixtures thereof.

9. A shampoo composition according to claim 8, wherein the anti-dandruff active is a pyridinethione salt.

10. A shampoo composition according to claim 9, wherein the pyridinethione salt is selected from the group consisting of zinc pyrithione, copper pyrithione, or mixtures thereof.

11. A shampoo composition according to claim 10, wherein the anti-dandruff active is zinc pyrithione.

12. A shampoo composition according to claim 8, wherein the anti-dandruff active is an azole.

13. A shampoo composition according to claim 12, wherein the anti-dandruff dandruff active is an imidazole selected from the group consisting of climbazole, ketoconazole, and mixtures thereof.

14. A method of treating hair and skin, said method comprising the step of applying to the hair and skin a shampoo composition according to claim 1.

* * * * *